United States Patent
Huh et al.

(10) Patent No.: US 12,064,834 B2
(45) Date of Patent: Aug. 20, 2024

(54) WELDING INFORMATION PROVIDING DEVICE

(71) Applicant: OTOS WING.CO., LTD., Seoul (KR)

(72) Inventors: Moon Young Huh, Seoul (KR); Sung Won Huh, Seoul (KR)

(73) Assignee: OTOS WING.CO., LTD., Seoul (KR)

(*) Notice: Subject to any disclaimer, the term of this patent is extended or adjusted under 35 U.S.C. 154(b) by 839 days.

(21) Appl. No.: 17/030,828

(22) Filed: Sep. 24, 2020

(65) Prior Publication Data

US 2021/0085524 A1    Mar. 25, 2021

(30) Foreign Application Priority Data

Sep. 24, 2019    (KR) .................. 10-2019-0117616

(51) Int. Cl.
*B23K 9/095*    (2006.01)
*B23K 9/32*    (2006.01)

(52) U.S. Cl.
CPC ............ *B23K 9/0956* (2013.01); *B23K 9/323* (2013.01)

(58) Field of Classification Search
CPC .............................. B23K 9/0956; B23K 9/323
See application file for complete search history.

(56) References Cited

U.S. PATENT DOCUMENTS

| | | |
|---|---|---|
| 6,557,174 B2 | 5/2003 | Martin et al. |
| 2013/0242110 A1 | 9/2013 | Terre et al. |
| 2016/0125653 A1 | 5/2016 | Denis |
| 2016/0163221 A1* | 6/2016 | Sommers ........... G02B 27/0172 434/234 |
| 2017/0289424 A1* | 10/2017 | Beeson ............... G02F 1/13318 |

(Continued)

FOREIGN PATENT DOCUMENTS

| | | |
|---|---|---|
| CN | 102793604 A | 11/2012 |
| CN | 107980153 A | 5/2018 |

(Continued)

OTHER PUBLICATIONS

Notice of Issuance dated Dec. 19, 2022 in Chinese Application No. 2020110103211.

(Continued)

*Primary Examiner* — Kyle M Lotfi
(74) *Attorney, Agent, or Firm* — Knobbe, Martens, Olson, & Bear, LLP

(57) ABSTRACT

This application relates to a welding information providing device. The device can provide a high-quality image that can easily identify a welding surrounding environment in addition to a portion adjacent to welding light by synthesizing images obtained under various photographing conditions. The device can also improve welding quality by providing an efficient guiding to an operator with respect to a current welding operation state. The device can include a cartridge unit that is located on a main body and selectively shields welding light, at least one camera unit that faces outward and obtains a welding image frame of a welding operation, and a sensor unit that detects a degree of light in at least a welding operation area. The device can also include an (Continued)

image display and a processor that provides a welding image generated through the welding image frame to the image display unit.

12 Claims, 19 Drawing Sheets

(56) References Cited

U.S. PATENT DOCUMENTS

| | | | |
|---|---|---|---|
| 2018/0130376 A1 | 5/2018 | Meess et al. | |
| 2018/0290226 A1 | 10/2018 | Huh | |
| 2019/0076297 A1 | 3/2019 | Huh | |
| 2020/0374510 A1* | 11/2020 | Berends | B23K 9/32 |

FOREIGN PATENT DOCUMENTS

| | | |
|---|---|---|
| DE | 20 2015 009 901 U1 | 5/2021 |
| KR | 10-2007-0064730 A | 6/2007 |
| KR | 10-2012-0091543 A | 8/2012 |
| KR | 10-1453001 B1 | 10/2014 |
| KR | 10-1673242 B1 | 11/2016 |
| KR | 10-2019-0029288 A | 3/2019 |
| WO | 2005/102230 A1 | 11/2005 |

OTHER PUBLICATIONS

Search Report dated Sep. 24, 2019 in Chinese Application No. 2020110103211.
Supplementary Search Report dated Sep. 24, 2019 in Chinese Application No. 2020110103211.
Preliminary Search Report dated Jan. 13, 2022 in French Application No. 2009556.
Examination Report dated Aug. 4, 2023 in Application No. GB2014977.9.
Examination Report dated Jan. 25, 2022 in Application No. GB2014977.9.
Intention to Grant dated Oct. 31, 2023 in Application No. GB2014977.9.
Notice of Allowance dated Aug. 20, 2021 in Korean Application No. 10-2019-0117616.
Office Action Report dated Nov. 22, 2021 in Chinese Application No. 2020110103211.
Office Action Report dated Aug. 3, 2022 in Chinese Application No. 2020110103211.
Office Action received in German Application No. 10 2020 211 788.8 dated Apr. 29, 2024.

\* cited by examiner

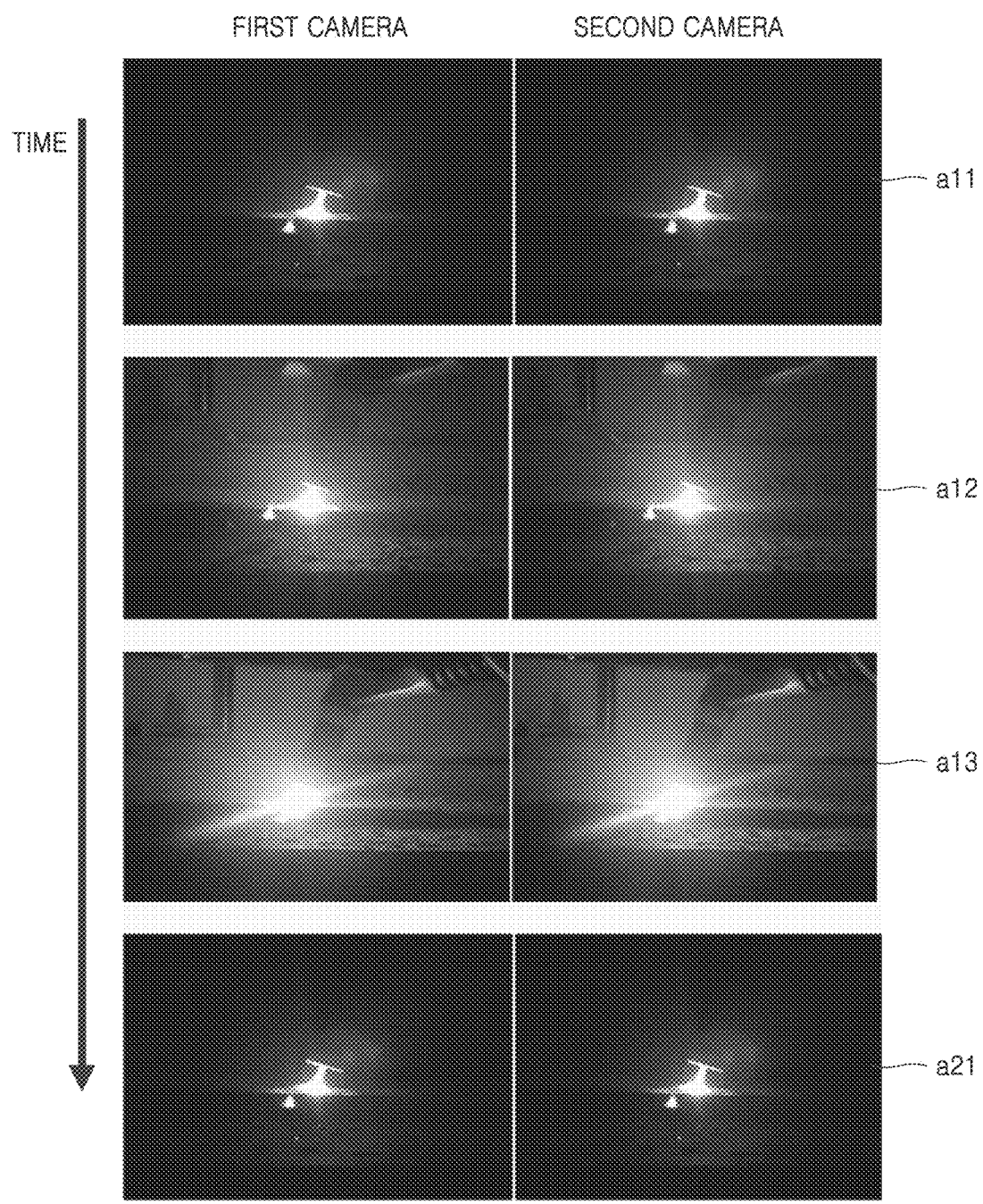

WELDING INFORMATION PROVIDING DEVICE

CROSS-REFERENCE TO RELATED APPLICATION

This application claims the benefits of Korean Patent Application No. 10-2019-0117616, filed on Sep. 24, 2019, in the Korean Intellectual Property Office, the disclosure of which is incorporated herein in its entirety by reference.

BACKGROUND

1. Field

One or more embodiments relate to a welding information providing device.

2. Description of Related Technology

Protective equipment is worn to protect operators from light, high heat, or the like produced during a welding process. Because an operator wearing protective equipment may only check that welding is performed through the protective equipment, the operator has to remove the protective equipment in order to check, with the naked eyes, various information for welding, such as conditions set in a welding device.

When a skill level of an operator is not high, especially when the operator wears an automatic welding helmet or a manual welding helmet, the operator may see only a portion adjacent to welding light and it is difficult for the operator to recognize a particular welding situation such as a surrounding environment of welding. Accordingly, it may be necessary to provide a high-quality image to the operator so that the operator checks even the welding surrounding environment and to provide detailed information with respect to welding state information to the operator.

The above situations may occur not only in welding operations, but also to medical staff in skin operations and/or medical treatments using camera images, and in other operations using camera images.

The disclosure of this section is to provide background Information relating to the invention. Applicant does not admit that any information contained in this section constitutes prior art.

SUMMARY

One or more embodiments include a welding information providing device for improving the welding accuracy of an operator by showing a welding surrounding environment as well as a welding spot to the operator.

One or more embodiments include a device for guiding information with respect to welding state information to an operator.

One or more embodiments provide accurate information to a user in an operation using camera images.

However, the embodiments disclosed herein are merely examples, and the scope of the disclosure is not limited thereto.

Additional aspects will be set forth in part in the description which follows and, in part, will be apparent from the description, or may be learned by practice of the presented embodiments of the disclosure.

According to one or more embodiments, a welding information providing device includes; a cartridge unit located on a main body and configured to selectively shield welding light; at least one camera unit located on the main body to look outward and configured to obtain a welding image frame of a welding operation; a sensor unit located outside the main body and including a module configured to detect a degree of light in at least a welding operation area; an image display unit located between the cartridge unit and a user inside the main body; and a processor configured to communicate with the cartridge unit, the at least one camera unit, and the image display unit and provide a welding image generated through the welding image frame to the image display unit.

The sensor unit may include a module configured to sense welding information, wherein the processor controls the image display unit to provide a guiding corresponding to the welding information based on the welding information sensed by the sensor unit.

At least a part of the sensor unit may be located on a welding torch.

The welding information may include at least one of welding speed information, welding direction information, welding temperature information, and distance information between a welding base material and a welding torch.

The cartridge unit may include a shield area for shielding the welding light, and the image display unit may include an image display area where an image is displayed to the user, wherein the shield area and the image display area overlap each other for the user's eye.

The image display unit may be configured to transmit light therethrough.

Other aspects, features, and advantages other than those described above will become apparent from the following detailed description, claims and drawings in which embodiments of the disclosure are shown.

BRIEF DESCRIPTION OF THE DRAWINGS

The above and other aspects, features, and advantages of certain embodiments of the disclosure will be more apparent from the following description taken in conjunction with the accompanying drawings.

FIG. 9 is a view for describing an example where a camera obtains an image according to an embodiment of the disclosure.

FIGS. 10A and 108 are views for describing an example where a processor synthesizes obtained images and improves the quality of a synthesized image according to an embodiment of the disclosure.

DETAILED DESCRIPTION

Figure 1:
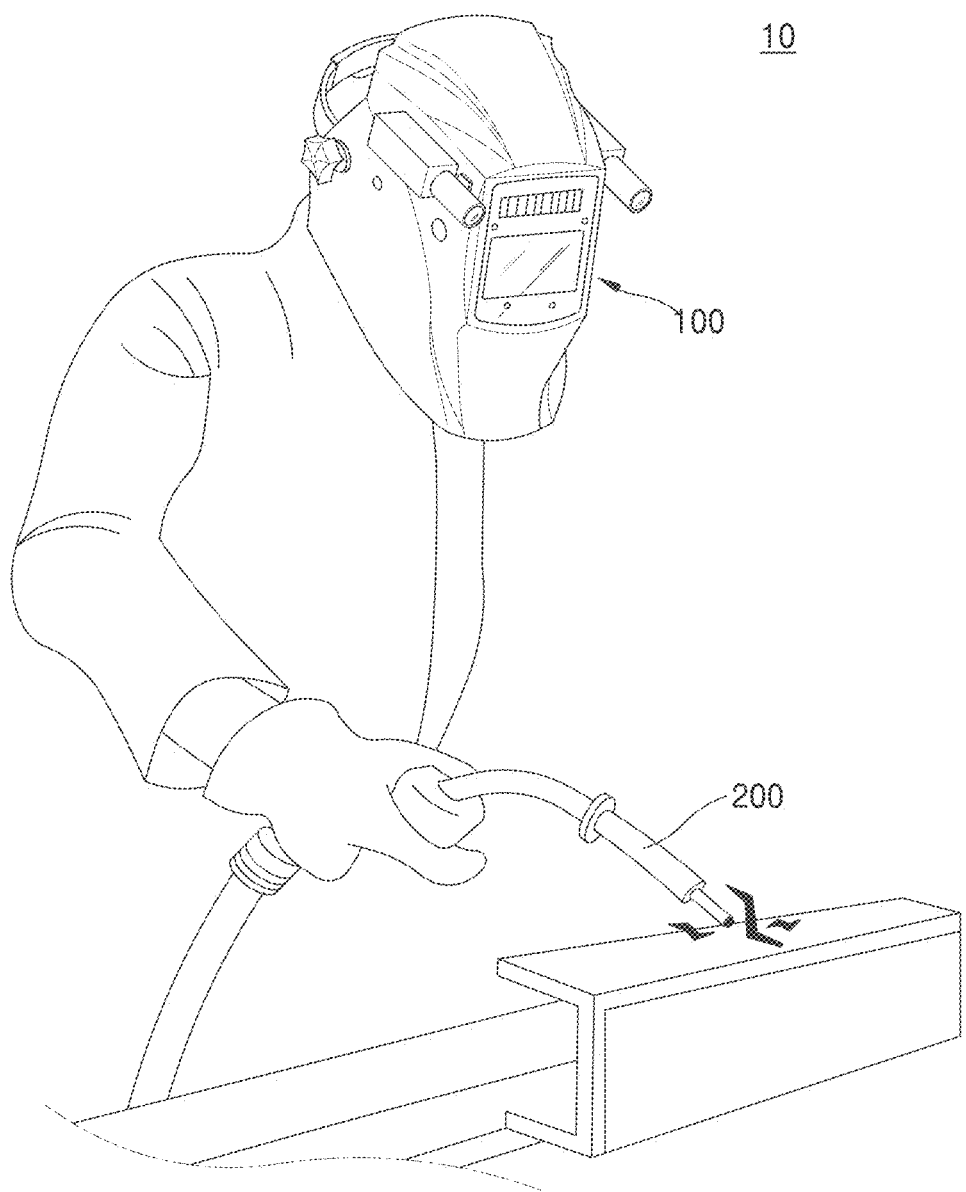
FIG. 1 is a view for describing a structure of a welding system according to an embodiment of the disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, various embodiments of the disclosure will be described with reference to accompanying drawings. As the disclosure allows for various changes and numerous embodiments, particular embodiments will be illustrated in the drawings and described in detail in the written description. However, this is not intended to limit the disclosure to particular modes of practice, and it is to be appreciated that all changes, equivalents, and substitutes that do not depart from the spirit and technical scope are encompassed in the disclosure. In the description of the drawings, like reference numerals in the drawings denote like elements.

In various embodiments of the disclosure, it is to be understood that the expressions such as "including" and "may include" are intended to indicate the existence of corresponding functions, actions, components, or the like disclosed in the disclosure, and are not intended to limit additional one or more functions, actions, components, or the like. In addition, in various embodiments of the disclosure, it is to be understood that the terms such as "including" "having," and "comprising" are intended to indicate the existence of features, numbers, steps, actions, components, parts, or combinations thereof disclosed in the specification, and are not intended to preclude the possibility that one or more other features, numbers, steps, actions, components, parts, or combinations thereof may exist or may be added.

In various embodiments of the disclosure, it will be understood that although the terms "first," "second," etc. may be used herein to describe various components, these components should not be limited by these terms. For example, the above terms do not limit the order and/or importance of the components. These terms are only used to distinguish one component from another. For example, a first user device and a second user device are both user devices and refer to different user devices. For example, a first component may be referred to as a second component, and similarly, a second component may be referred to as a first component, without departing from the scope of various embodiments of the disclosure.

It will be understood that when a component is referred to as being "connected to" or "mounted on" another component, the component may be directly connected to the other component or may be connected to the other component with an intervening component therebetween. On the other hand, it will be understood that when a component is referred to as being "directly connected to" or "directly mounted on" another component, intervening components may not be present therebetween.

In an embodiment of the disclosure, the terms such as "unit" or "part" are terms used to refer to a component configured to perform at least one function or operation, and these components may be implemented in hardware or software, or a combination of hardware and software. In addition, except a case where each of a plurality of "units" or "parts" is required to be implemented in individual particular hardware, the plurality of "units" or "parts" may be integrated into at least one module or chip and implemented in at least one processor.

Terms such as those defined in commonly used dictionaries should be interpreted as having meanings consistent with meanings in the context of related technologies, and will not be interpreted as having ideal or excessively formal meanings unless explicitly defined in various embodiments of the disclosure, Hereinafter, various embodiments of the disclosure will be described in detail with reference to the accompanying drawings.

FIG. 1 is a view for describing a structure of a welding system according to an embodiment of the disclosure.

Referring to FIG. 1, a welding system 10 of the disclosure may include a welding information providing device 100 and a welding torch 200. The welding information providing device 100 and the welding torch 200 may be connected to each other through a communication network to transmit and receive data. The welding information providing device 100 and the welding torch 200 may operate by being matched in a one-to-one manner, but are not limited thereto. The welding information providing device 100 and the welding torch 200 may operate by being matched in a one-to-n manner, in which n is a number equal to or greater than 2. In an example, multiple welding torches (n welding torches) 200 may be connected to one welding information providing device 100, or one welding torch 200 may be connected to multiple welding information providing devices (n welding information providing devices) 100. In addition, the welding information providing device 100 and the welding torch 200 may communicate with a separate server to exchange data, The welding information providing device 100 may provide information about a welding situation to an operator. In detail, the welding information providing device 100 may obtain welding images by using at least one camera unit mounted on the welding information providing device 100, may generate a composite image based on the obtained welding images, and may display the composite image to the operator. In this case, the welding information providing device 100 may generate a synthesized welding image by using high dynamic range (HDR) technology, and may display and provide a high-quality welding image to the operator. In this case, the operator may visually check, through the high-quality welding image, information about a shape of a weld bead and a surrounding environment other than a portion adjacent to welding light.

The welding information providing device 100 according to an embodiment of the disclosure may obtain image frames through two or more camera units to synthesize and provide a high-quality welding image, and may display an image generated through each image frame on at least one display unit. In this case, the welding information providing device 100 may synthesize images by repeatedly photographing using different shutter speeds. International Organization for Standardization (ISO) sensitivities, and gain values of cameras. The welding information providing device 100 according to an embodiment of the disclosure may improve image quality through contrast enhancement on the obtained synthesized image.

Also, the welding information providing device 100 may provide a function of displaying welding information in a preferred color (e.g., green or blue) by using red, green, and blue (RGB). Furthermore, the welding information providing device 100 of the disclosure may provide a magnifier power correction function (e.g., enlargement and reduction of a screen). Also, the welding information providing device 100 of the disclosure may provide a temperature-synthesized image by using a separate thermal imaging camera. In this case, the welding information providing device 100 may display a welding temperature in color. The welding information providing device 100 of the disclosure may support a function of providing sound (e.g., a guidance alarm) or a guidance voice for all of the functions described above.

The welding torch 200 according to an embodiment of the disclosure may sense, by using at least one sensor, a welding situation including a welding temperature, a welding direction, a welding slope, a welding speed, and an interval between a base material and the welding torch 200 in a real-time welding operation. The welding torch 200 may monitor a state of the welding torch 200 and may change a setting value of a welding torch operation according to the welding situation.

The welding information providing device 100 of the disclosure may receive information about an operation setting and an operation state from the welding torch 200 through a communication network connected to the welding torch 200, and may provide operation information to the operator based on the received welding information through visual feedback.

For example, when the welding information providing device 100 receives sensing information about a welding temperature value, the welding information providing device 100 may output a notification corresponding to the welding temperature value in any of various methods such as light, a vibration, or a message. In this case, the notification may be visual feedback provided on a display unit of the welding information providing device 100, or may be auditory feedback through sound (e.g., a guidance alarm) or a guidance voice.

The sensing information about the welding temperature value may include information about whether a welding temperature exceeds a preset temperature range. In addition, the sensing information about the welding temperature value may include a numerical value, a grade, a level, or the like corresponding to a temperature value of a welding helmet.

When the welding information providing device 100 according to an embodiment of the disclosure determines that temperature values of the welding torch 200 and the welding helmet exceed a preset temperature range, the welding information providing device 100 may guide the operator to stop a welding operation. When a temperature value of welding exceeds a preset temperature range, image quality may be deteriorated. Accordingly, the welding information providing device 100 may guide the operator to adjust the temperature value of the welding torch 200.

When a current or voltage state of the welding torch 200 is sensed as abnormal, the welding information providing device 100 according to an embodiment of the disclosure may provide visual feedback for warning.

In this case, the visual feedback may involve providing an icon indicating danger on a portion of the image display unit of the welding information providing device 100 that is displaying an operation site. As another example, the welding information providing device 100 may provide an operation suspension guiding through visual feedback by repeatedly increasing and decreasing a chroma of a particular color (e.g., red) on the entire image display unit.

According to an embodiment of the disclosure, the welding information providing device 100 may sense welding information by using at least one sensor (e.g., a second sensor) included in the welding torch 200 as well as a sensor (e.g., a first sensor) included in the welding information providing device 100. In this case, the welding information providing device 100 may sense, through at least one sensor, a welding situation including a light intensity, a welding temperature, a welding direction, a welding slope, a welding speed, and an interval between a base material and the welding torch 200 related to a real-time welding operation.

Likewise, the welding information providing device 100 may provide a guide corresponding to welding information based on the welding information sensed by the sensor (e.g., the first sensor) included in the welding information providing device 100.

According to an embodiment of the disclosure, the welding information providing device 100 may change a movement of the welding torch 200 by sensing a preset user movement or a preset user voice after the operation suspension guiding is provided.

In another embodiment, when communication between the welding information providing device 100 and the welding torch 200 is not smooth, the welding information providing device 100 may obtain temperature values of the welding torch 200 and a welding portion through an image sensor provided therein. For example, the welding information providing device 100 may obtain temperature values of the welding torch 200 and the welding helmet based on image data obtained through a thermal imaging camera.

Although information received from the welding torch 200 is welding temperature information in the above embodiment, the welding information providing device 100 may provide various guidings for various welding information.

Figure 2:
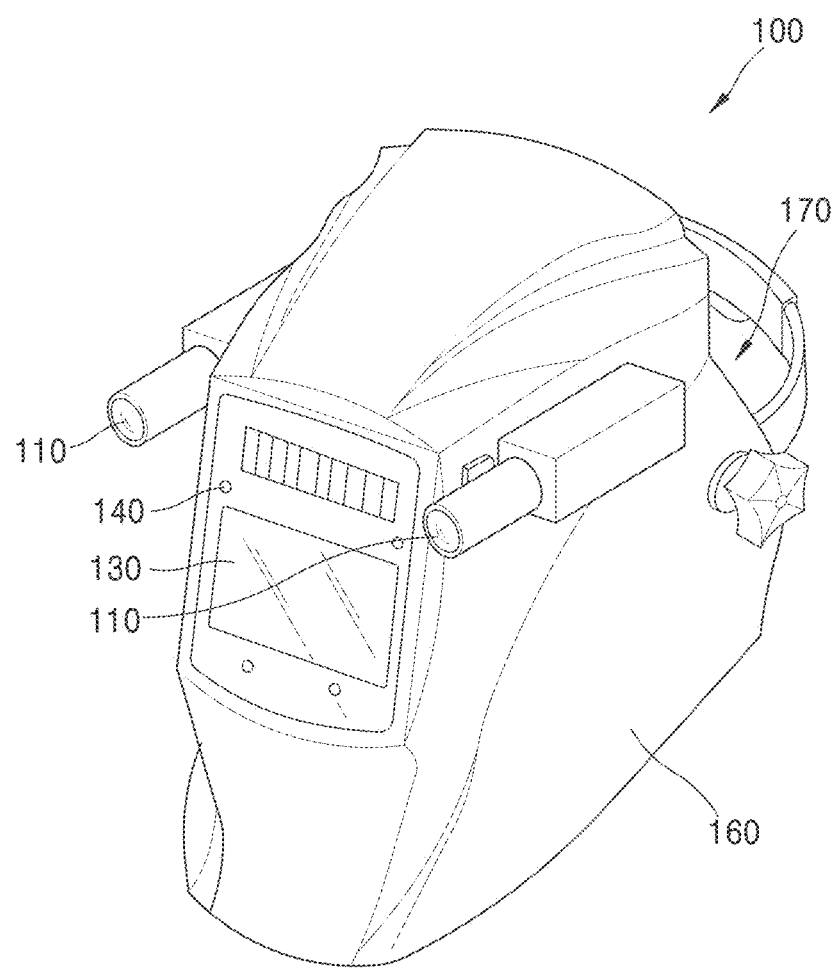
FIG. 2 is a perspective view of the welding information providing device according to an embodiment of the disclosure.

FIG. 2 is a perspective view of the welding information providing device 100 according to an embodiment of the disclosure.

Referring to FIG. 2, the welding information providing device 100 according to an embodiment of the disclosure may include a main body 160, a cartridge unit 130 provided on the main body 160, at least one camera unit 110 mounted on a side of a front portion of the main body 160, at least one sensor unit 140 provided outside the main body 160, a fixing portion 170 located on a rear surface of the main body 160 and fixing the welding information providing device 100 to the head of an operator, an image display unit provided inside the main body 160, and a processor connected to the cartridge unit 130, the camera unit 110, the sensor unit 140, and the image display unit to enable communication. The main body 160 that protects the operator's face may include a material having a certain strength, for example, reinforced plastic, but the disclosure is not limited thereto. The main body 160 may include any of various materials as long as it is resistant to elements such as sparks that may occur during welding.

The fixing portion 170 directly contacts the head of the operator, and at least a portion of a side surface of the fixing portion 170, for example, an inner surface of the fixing portion 170 that directly contacts the head of the operator, may include a soft material such as a fiber material or a cushioning material.

Figure 3A:
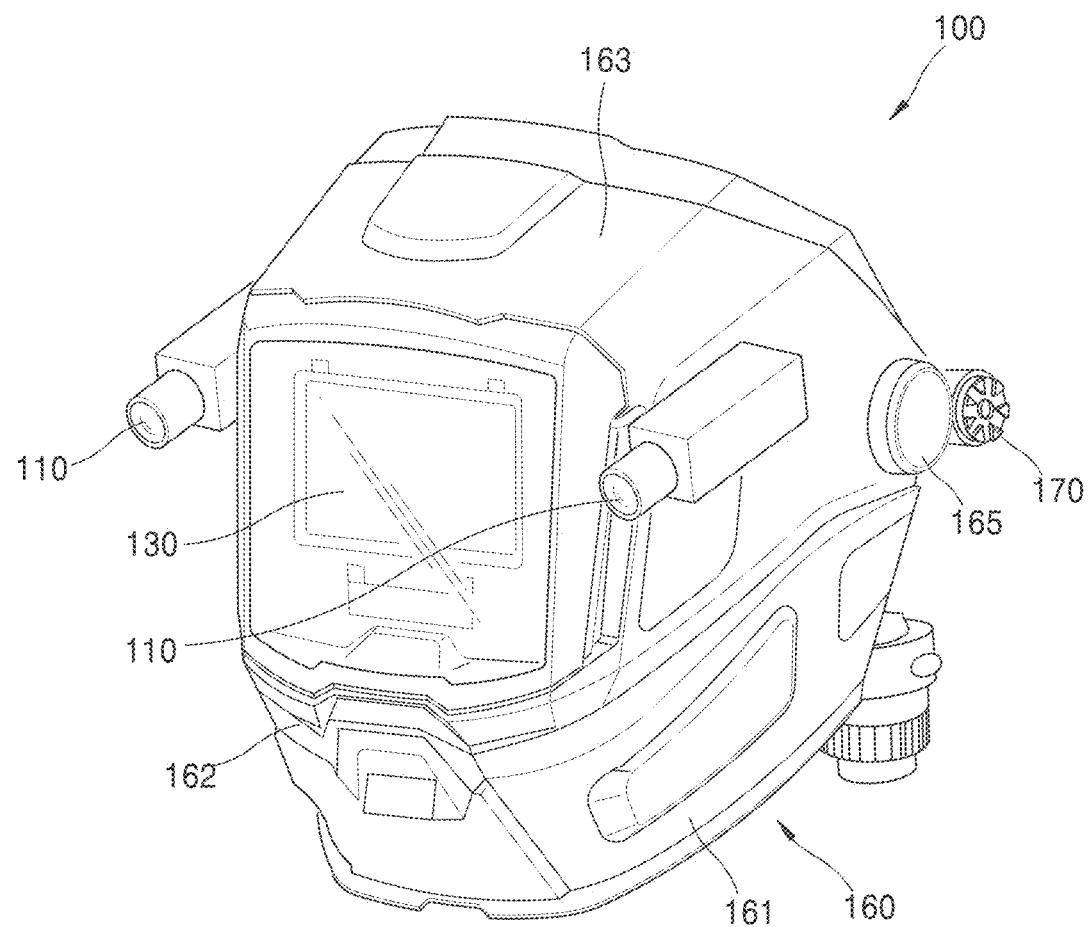
FIGS. 3A, 3B and 3C are perspective views of the welding information providing device according to another embodiment of the disclosure.
Figure 3B:
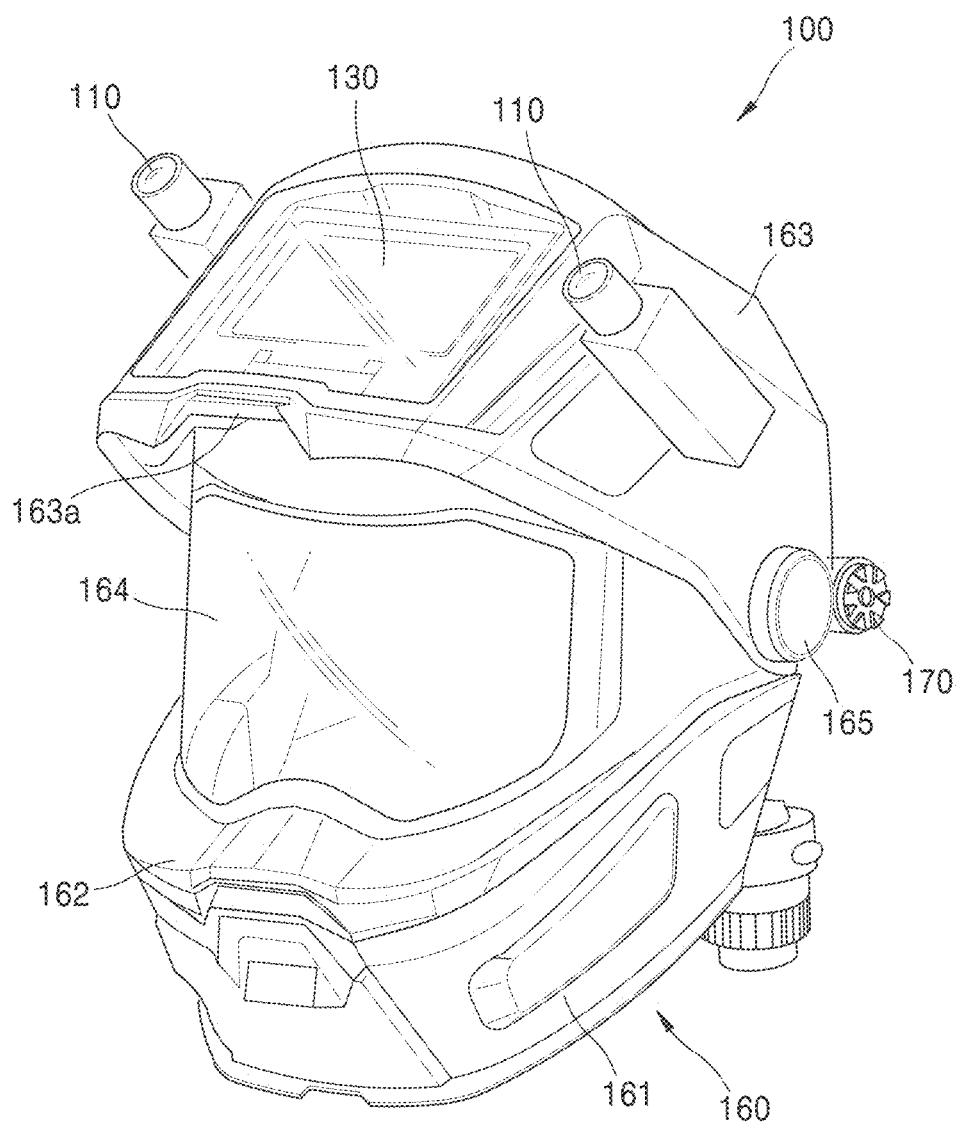
Figure 3C:
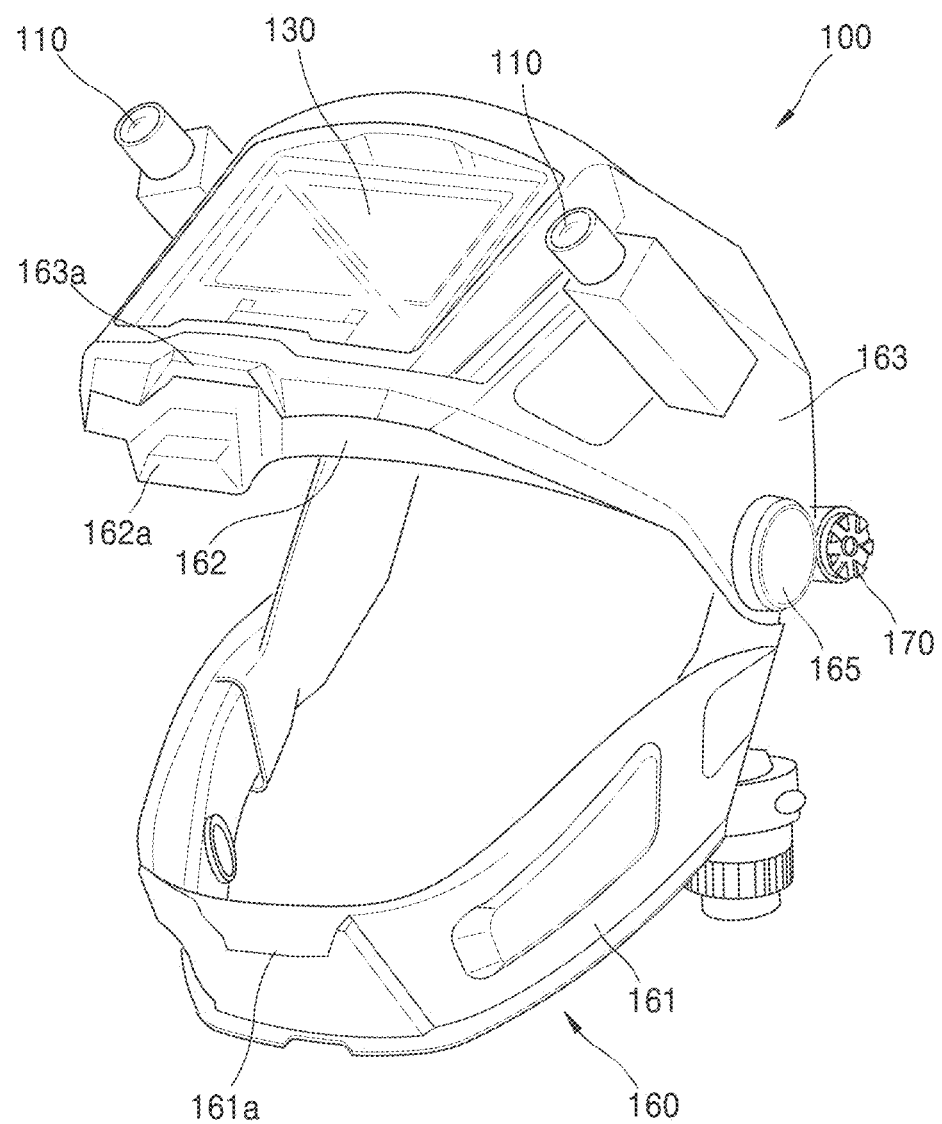

FIGS. 3A through 3C illustrate the welding information providing device 100 according to another embodiment of the disclosure.

Referring to FIGS. 3A through 3C, the main body 160 of the welding information providing device 100 according to another embodiment of the disclosure may include a first main body 161, a second main body 162, and a third main body 163, wherein the first main body 161, the second main body 162, and the third main body 163 are detachably coupled to one another. Ends of the first main body 161 through the third main body 163 are coupled by a hinge portion 165. The first main body 161 through the third main body 163 are coupled to one another to pivot about the hinge portion 165.

The first main body 161 may be located around the chin of a user, and may extend to be thick enough to protect the chin and/or the neck of the user. A position of the first main body 161 may be fixed.

The second main body 162 may he coupled to an upper end of the first main body 161 and may extend to the top of the user's head to have an opening corresponding to the user's face. A protective surface 164 may be provided in the opening of the second main body 162, as shown in FIG. 3B, and the protective surface 164 may include a light-transmitting reinforcement material. Accordingly, the user may observe the outside through the protective surface 164 and the user's face may be protected by the protective surface 164. The protective surface 164 may have a certain degree of light filtering function.

The third main body 163 may be provided to cover a front surface of the second main body 162, and may extend to the top of the user's head from the user's face. The cartridge unit 130, the sensor unit 140, the camera unit 110, and the image display unit may be mounted on the third main body 163.

A first coupling portion 161a is provided on the first main body 161, a second coupling portion 162a is provided on the second main body 162, and a third coupling portion 163a is provided on the third main body 163.

The first coupling portion 161a and the second coupling portion 162a are selectively coupled to each other, and the second coupling portion 162a and the third coupling portion 163a are selectively coupled to each other.

FIG. 3A illustrates a state where the first coupling portion 161a and the second coupling portion 162a are coupled to each other and the second coupling portion 162a and the third coupling portion 163a are coupled to each other. Accordingly, the user's face is protected by the third main body 163, and the cartridge unit 130 is located to correspond to the user's eyes. In this case, the user performs a welding operation.

FIG. 3B illustrates a state where the second coupling portion 162a and the third coupling portion 163a are decoupled and the first coupling portion 161a and the second coupling portion 162a are coupled to each other. In this state, the user may observe an operation site during operation. In this case, because the protective surface 164 still faces the user's face, the user's face may be protected from an external environment. Air may be continuously supplied by a separate ventilation unit into an inner space inside the protective surface 164. This also applies to the state of FIG. 3A. An operation such as inspection of the welding operation during the welding operation may be performed in this state.

FIG. 3C illustrates a state where the first coupling portion 161a and the second coupling portion 162a are decoupled and the second coupling portion 162a and the third coupling portion 163a are coupled to each other. In this state, the user's face may be exposed, and the user may more freely communicate with others or observe a surrounding environment without taking off the main body 160.

According to FIGS. 3A through 3C, the user may adjust a degree of opening of the main body 160 according to an operation situation, thereby further improving operation convenience.

Figure 4:
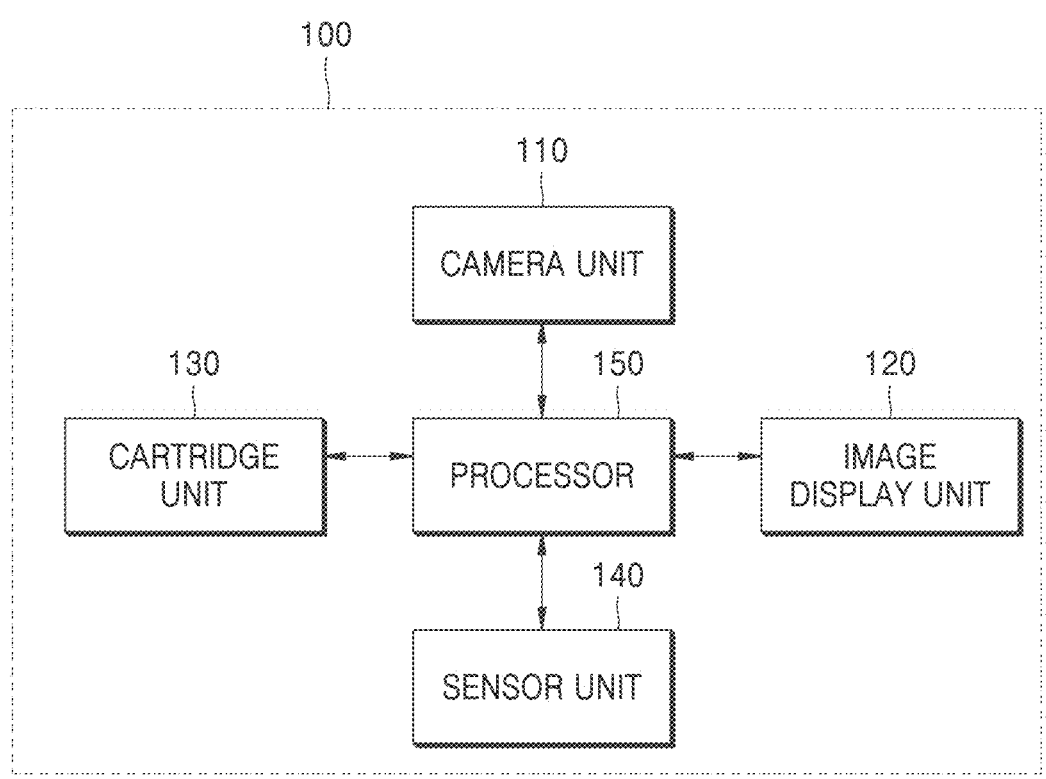
FIG. 4 is a block diagram for describing elements of the welding information providing device according to an embodiment of the disclosure.

FIG. 4 is a block diagram for describing elements of the welding Information providing device 100 according to an embodiment of the disclosure.

The camera unit 110 may include at least one camera device, and may include a camera for obtaining an image of a welding operation site. According to an embodiment of the disclosure, cameras of the camera unit 110 may be symmetrically mounted on both side surfaces of the main body 160. For example, a first camera and a second camera of the camera unit 110 may be symmetrically mounted on areas of both sides of a front portion of the welding information providing device 100. In embodiments, when an odd number of cameras of the camera unit 110 are provided, the cameras may be mounted on an upper end of a central portion of the main body 160.

The camera unit 110 may receive a control command from the processor 150, and may photograph the welding operation site by changing settings such as a shutter speed, an ISO sensitivity, and a gain in response to the control command. The camera unit 110 may include the first camera and the second camera, and the first camera and the second camera may photograph the welding operation site through different photographing settings.

The camera unit 110 according to an embodiment of the disclosure may be provided on areas of both sides of a front portion of the main body 160.

The cartridge unit 130 may be located on the front portion of the main body 160, and the cartridge unit 130 may be arranged at a front side to which the user's gaze is directed. In detail, the cartridge unit 130 may be mounted in an opening formed in the front portion of the main body 160, and may be located in a path through which welding light reaches the user. The cartridge unit 130 may selectively shield welding light generated during a welding operation from reaching the user who is an operator as described below. In embodiments, the cartridge unit 130 may be provided to increase a light-shielding degree through darkening based on welding light information sensed by the sensor unit 140, for example, a photo sensor. In this case, according to an embodiment of the disclosure, the cartridge unit 130 may include, for example, a liquid crystal display (LCD) panel in which a degree of darkening may be adjusted according to an alignment direction of liquid crystals. However, the disclosure is not limited thereto, and the cartridge unit 130 may be implemented as any of various panels such as a vertical alignment (VA) LCD, a twist nematic (TN) LCD, or an in-plane switching (IPS) LCD.

A degree of darkening of the cartridge unit 130 may be automatically adjusted by the processor 150 according to a brightness of welding light. When a degree of darkening is automatically adjusted according to a brightness of welding light as described above, the sensor unit 140 may be used. When the sensor unit 140 senses light intensity of welding light to obtain welding light information, and transmits, as an electrical signal, information about the light intensity of the welding light included in the welding light information to the processor 150, the processor 150 may control a degree of darkening based on the light intensity of the welding light.

In embodiments, the cartridge unit 130 may change in real time a light-shielding degree of a panel to correspond to an intensity of light generated at the welding operation site.

Although cameras of the camera unit 110 are provided at both sides of the cartridge unit 130 in FIGS. 2 through 3C, the disclosure is not limited thereto, and the cartridge unit 130 may be provided on a front portion of the camera unit 110 and a welding image in which light is shielded by the cartridge unit 130 may be obtained by the camera unit 110. The camera unit 110 according to an embodiment of the disclosure may include a thermal imaging camera. The welding information providing device 100 may obtain a temperature image by synthesizing a thermal image obtained by the thermal imaging camera with an image of the welding operation site.

According to an embodiment of the disclosure, a lighting unit electrically connected to the processor 150 may be further provided. The lighting unit is located outside the welding information providing device 100 and is configured to emit light to at least a welding operation area. The lighting unit may include a plurality of light-emitting diode (LED) modules, and an output level of fight emitted through the lighting unit may be automatically adjusted according to the amount of external light under the control of the processor 150. According to an embodiment of the disclosure, the lighting unit may operate in conjunction with the camera unit 150 under the control of the processor 150.

In embodiments, a separate communication unit may be provided to receive welding information from the welding torch 200 therethrough and transmit a command for controlling the welding torch 200. According to an embodiment of the disclosure, the communication unit may transmit a synthesized image to an external device other than the welding torch 200. In this case, the external device may include any of various devices including a communication module such as a smartphone or a computer of an operator/third party.

The communication unit may perform communication with various external devices according to various communication methods. The communication unit may include at least one of a Wi-Fi chip, a Bluetooth chip, a wireless communication chip, and a near-field communication (NFC) chip. In particular, when the Wi-Fi chip or the Bluetooth chip is used, the communication unit may first transmit and receive various connection information such as a service set identifier (SSID)) or a session key to establish a communication connection by using the various connection information, and then may transmit and receive various information. The wireless communication chip refers to a chip that performs communication according to various communication standards such as Institute of Electrical and Electronics Engineers (IEEE), Zigbee, 3rd Generation (3G), 3rd Generation Partnership Project (3GPP), or Long-Term Evolution (LTE). The NFC chip refers to a chip that operates in an NFC method using 13.56 MHz among various radio frequency identification (RFID) frequency bands such as 135 kHz, 13.56 MHz, 433 MHz, 860 to 960 MHz, or 2.45 GHz.

The sensor unit 140 may include a plurality of sensor modules configured to sense various information about a welding site and obtain welding information. In this case, the welding information may include a welding temperature, a welding direction, a welding slope, a welding speed, and an interval between a base material and the welding torch 200 in a real-time welding operation. Moreover, the sensor unit 140 may include an optical sensor module configured to detect a degree of light at least within the welding operation area.

According to an embodiment of the disclosure, the sensor unit 140 may include an illuminance sensor, and in this case, the sensor unit 140 may obtain information about a light intensity of welding light at the welding site. The sensor unit 140 may further include various sensors such as a proximity sensor, a noise sensor, a video sensor, an ultrasonic sensor, and an RF sensor in addition to the illuminance sensor, and may sense various changes related to a welding operation environment.

The processor 150 may generate a high-quality synthesized image by synthesizing welding image frames received through the camera unit 110. The processor 150 may differently set photographing conditions for frames of the camera unit 110 and may obtain a synthesized image by synthesizing frames obtained in a chronological order in parallel. In detail, the processor 150 may control the camera unit 110 to photograph the welding operation site by changing a shutter speed, an ISO sensitivity, a gain, etc. of the camera unit 110.

In this case, the processor 150 may differently set a photographing condition according to conditions such as welding light and ambient light of the welding site, and a degree of movement of the welding torch 200. In detail, the processor 150 may set the photographing condition to reduce the ISO sensitivity and the gain as the welding light and/or the ambient light of the welding site increases. Also, the processor 150 may set the photographing condition to increase the shutter speed when the movement and/or operation speed of the welding torch 200 is sensed as fast.

The processor 150 may synthesize images of a preset number of frames in parallel. According to an embodiment of the disclosure, the images in the preset frames may be obtained under different photographing conditions.

When two or more camera units 110 are provided, the processor 150 according to an embodiment of the disclosure may control the camera units 110 to photograph the welding operation site by differently setting photographing conditions of cameras. Even in the case, the processor 150 may also synthesize images of a preset number of frames in parallel.

The processor 150 may control an overall operation of the welding information providing device 100 by using various programs stored in a memory. For example, the processor 150 may include a central processing unit (CPU), random-access memory (RAM), read-only memory (ROM), and a system bus. The ROM is an element in which a set of instructions for system booting are stored, and the CPU copies an operating system in the memory of the welding information providing device 100 to the RAM according to the instructions stored in the ROM, and boots the system by executing the operating system. When the booting is completed, the CPU may copy various applications stored in the memory to the RAM, and may perform various operations by executing the various applications. Although the processor 150 includes only one CPU in the above, the disclosure is not limited thereto, and the processor 150 may include a plurality of CPUs (digital signal processors (DSPs) or system-on-chips (SoCs)).

According to an embodiment of the disclosure, the processor 150 may be implemented as a DSP, a microprocessor, and/or a time controller (TCON). However, the processor 150 is not limited to thereto, and may include one or more of a CPU, a micro-controller unit (MCU), a micro-processing unit (MPU), a controller, an application processor (AP), a communication processor (CP), and an advanced RISC machine (ARM) processor, or may be defined by corresponding terms. Also, the processor 150 may be implemented as an SoC or a large scale integration (LSI) in which a processing algorithm is embedded, or may be implemented as a field-programmable gate array (FPGA).

According to an embodiment of the disclosure, the image display unit 120 may be located in the main body 160, and the image display unit 120 of the present embodiment of the disclosure may display a synthesized welding image to the operator toward the operator's face. Also, the image display unit 120 may display a user interface (UI) for a current state such as a battery state of the welding information providing device 100 when a preset event occurs.

Figure 5:
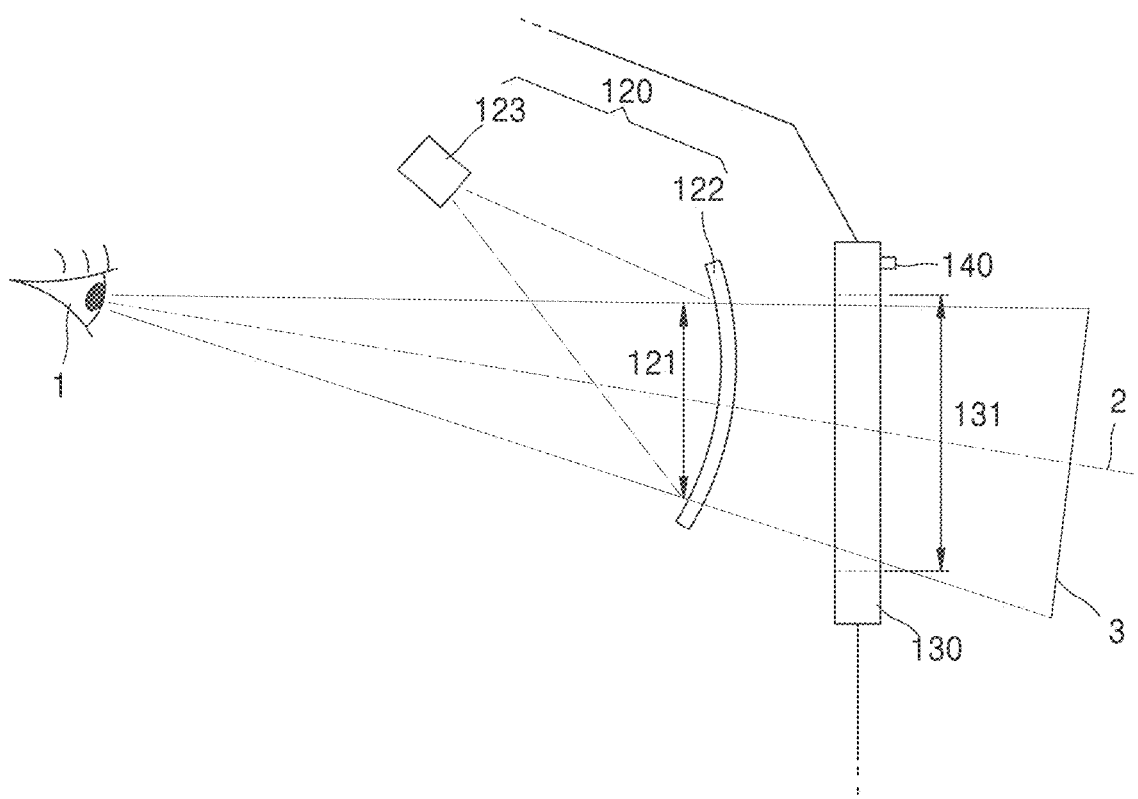
FIG. 5 is a view for describing an image display unit according to an embodiment of the disclosure.

FIG. 5 is a view, illustrating the inside of the main body 160, for describing the image display unit 120 according to an embodiment of the disclosure.

The cartridge unit 130 for selectively shielding welding light is located in front of a users eye 1 located inside the main body 160.

The cartridge unit 130 may include a shield area 131 for shielding welding light, and may protect the user's eye 1 from the welding light introduced into the main body 160 through the shield area 131.

The image display unit 120 is located between the eye 1 and the cartridge unit 130.

According to an embodiment of the disclosure, the image display unit 120 may include an image emission module 123 and a screen module 122.

The image emission module 123 is electrically connected to the processor 150, receives welding image data transmitted from the processor 150, and emits a welding image to the screen module 122.

In an embodiment of the disclosure, a liquid crystal display device, an organic electroluminescent (EL) device, an inorganic EL device, a micro-LED device, a digital light processing (DLP) device, or a liquid crystal on silicon (LCOS) device may be used as the image emission module 123.

When an operator wears the main body 160 thereon, an inner space between a front portion of the main body 160 and the operator's face is very narrow, and thus the image emission module 123 may be located in a space between an inner surface of the front portion of the main body 160 and an upper end portion (near the forehead) of the operator's face.

In an embodiment of the disclosure, a light exit surface of the image emission module 123 may face the screen module 122, and the image emission module 123 may include an optical path curving portion and may curve an optical path at least once so that an image is emitted to the screen module 122, thereby efficiently using a narrow space between the front portion of the main body 160 and the operator's face (e.g., near the forehead). The optical path curving portion may include a reflector such as a reflective mirror. Alternatively, the optical path curving portion may include an optical fiber or the like.

Initial image light is emitted from the image emission module 123 to the screen module 122. The screen module 122 may be located adjacent to the cartridge unit 130, and may be located in a path of welding light between the eye 1 and the cartridge unit 130.

The screen module 122 may project the incident initial image light to generate a virtual image 3 outside the main body 160. The operator may visually check a welding operation through the virtual image 3. A welding operation image included in the virtual image 3 is the same as a welding operation image included in the initial image. The virtual image 3 may be located at a certain distance from the operator's eye 1, and the certain distance may be selected in a range from about 10 cm to about 1 m. A size of the virtual image 3 may be greater than that of the initial image, and, for example, a magnification of the virtual image 3 with respect to the initial image may range from about 1.1 to 20.

The screen module may have a concave shape, and a concave surface of the screen module 122 may face the operator's eye 1. According to an embodiment of the disclosure, the screen module 122 may be aspherical. Because the screen module 122 is aspherical, distortion may be prevented from occurring when a magnification is increased.

An image display area 121 where an image is displayed to the user by the screen module 122 overlaps the shield area 131 for the user's eye 1. In embodiments, the user may see an external environment including a welding operation area through the shield area 131, and thus the shield area 131 corresponds to a field of view of the user. The image display area 121 may be an area where a welding image of the welding operation area obtained by the camera unit 110 is projected, and the user may see the welding image that is the virtual image 3 through the image display area 121. The virtual image 3 formed through the image display area 121 may exist within the shield area 131 corresponding to the Meld of view, without exceeding a range of the shield area 131. The user may selectively see the outside through the shield area 131 or see the outside through the image display area 121 as described below, and the user may secure a field of view through an image which is slightly less than a field of view through the shield area 131. This structure may also apply to other embodiments of the disclosure.

The screen module 122 may allow light to be transmitted therethrough. According to an embodiment of the disclosure, a member formed of a glass or plastic material may be used as the screen module 122. Accordingly, the user may see the outside through the screen module 122 and the cartridge unit 130 when the image emission module 123 is turned off.

Figure 6:
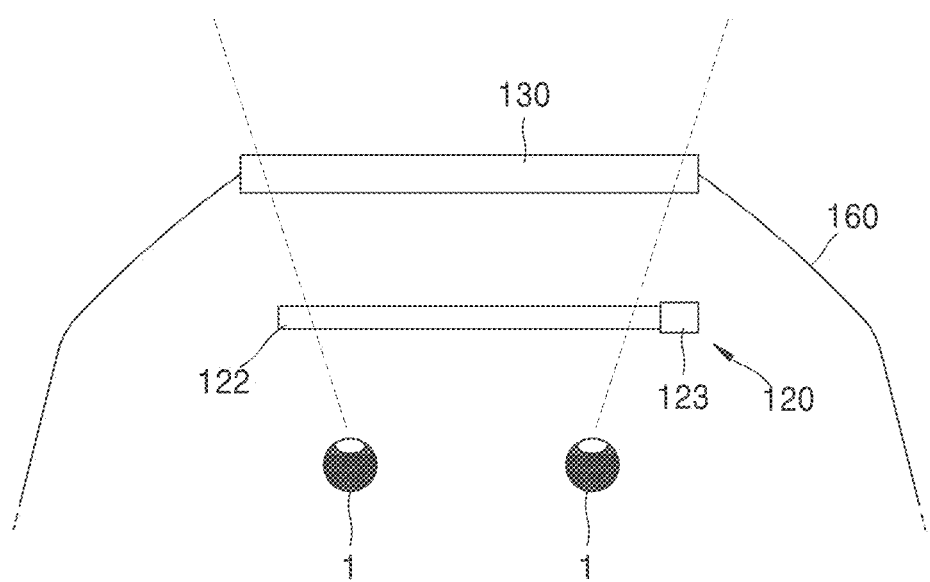
FIG. 6 is a view of the image display unit according to another embodiment of the disclosure.

FIG. 6 is a view of the image display unit 120 according to another embodiment of the disclosure.

Referring to FIG. 6, the image display unit 120 according to another embodiment of the disclosure may include the screen module 122 and the image emission module 123, and the image emission module 123 is coupled to a side surface of the screen module 122. Accordingly, the image emission module 123 may emit an image from the side surface of the screen module 122 to the screen module 122, and thus a welding image may be projected to the screen module 122.

Figure 7:
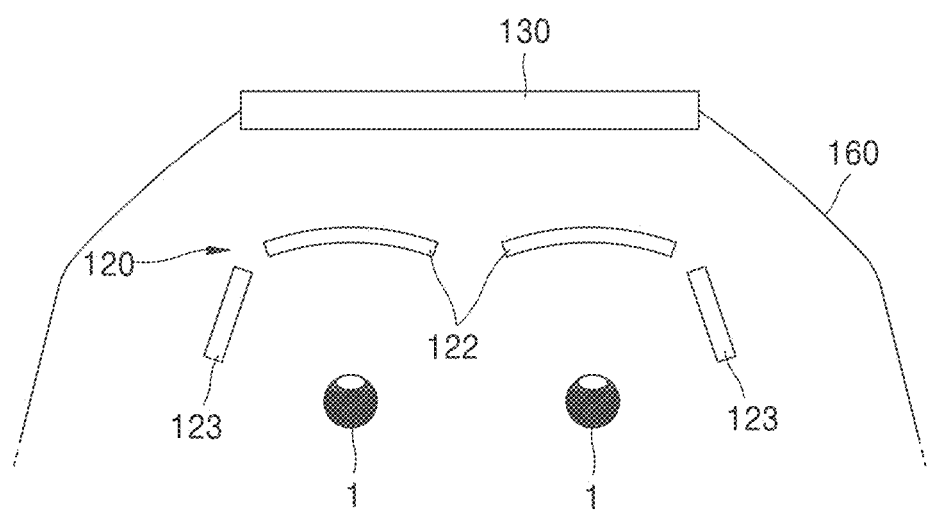
FIG. 7 is a view of the image display unit according to another embodiment of the disclosure.

FIG. 7 is a view of the image display unit 120 according to another embodiment of the disclosure.

Referring to FIG. 7, the image display unit 120 according to another embodiment of the disclosure may be provided as a glasses type, the image emission module 123 may be located at a portion corresponding to each leg, and an image may be formed through the screen module 122. Although the image emission modules 123 are located at both sides of the eye 1 in FIG. 6, the disclosure is not limited thereto and the image emission module 123 may be located only at a side of the eye 1.

Although the image display unit 120 includes the screen module 122 and the image emission module 123 in the above embodiment, the disclosure is not limited thereto. For example, the image display unit 120 may include an eyepiece display located adjacent to the user's eye 1. An eyepiece part may be provided adjacent to the eyepiece display, and the user may check a welding image formed on the eyepiece display in a state where the eyepiece part is in close contact with the user's face. Each eyepiece part may include a lens unit, and the lens unit may enlarge a high-quality synthesized image formed on the eyepiece display so that an image is easily formed on the user's eye. The eyepiece display may be a transparent display.

According to an embodiment of the disclosure, the image display unit 120 may display a welding image synthesized based on an image obtained by the camera unit 110 corresponding to each eye on the eyepiece display corresponding to each eye.

For example, when a first camera mounted in an area corresponding to the left eye obtains an image under a first photographing condition, the image display unit 120 may display a first synthesized image synthesized based on the first photographing condition on a first eyepiece display included in the area corresponding to the left eye on a rear portion of the image display unit 120. Likewise, when a second camera mounted in an area corresponding to the right eye obtains an image under a second photographing condition, the image display unit 120 may display a second synthesized image synthesized based on the second photographing condition on a second eyepiece display included in the area corresponding to the right eye on the rear portion of the image display unit 120.

In this case, a flexible synthesized image with a three-dimensional effect may be provided, when compared to a case where the same synthesized image is displayed to both eyes. However, this is merely an example, and the eyepiece displays may display the same synthesized image even when the camera units 110 respectively corresponding to the eyepiece displays perform photographing under different conditions.

According to an embodiment of the disclosure, the processor 150 may enable information to be selectively obtained through the cartridge unit 130 or the camera unit 110.

Figure 8:
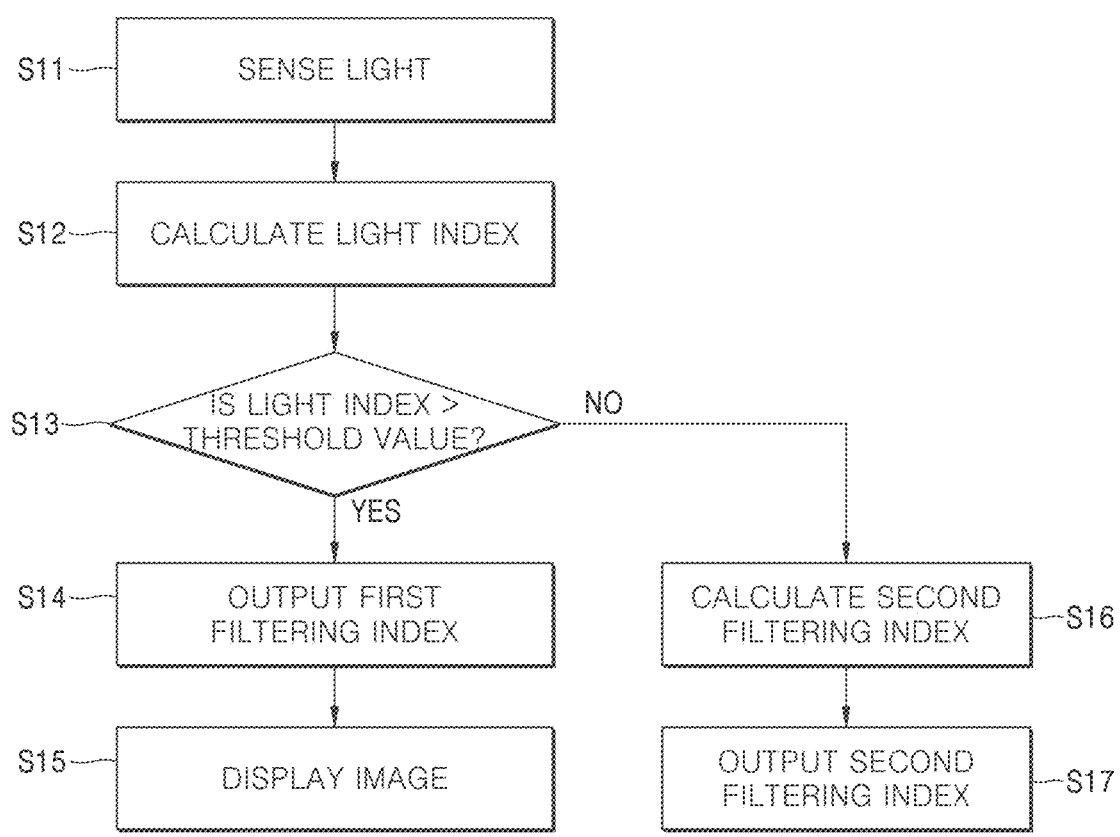
FIG. 8 is a flowchart of a method, performed by a processor, of providing welding information according to an embodiment of the disclosure.

FIG. 8 is a flowchart of a method, performed by the processor 150, of providing welding information according to an embodiment of the disclosure.

The sensor unit 140 may sense a degree of light in a welding operation site (S11). According to an embodiment, the sensor unit 140 may include an illuminance sensor module, and thus the degree of light may correspond to illuminance data in the welding operation area. The processor 150 may sense a degree of light by using a sensor unit included in the welding torch 200.

When data about the degree of light is transmitted to the processor 150, the processor 150 calculates a light index in the welding operation area based on the data (S12). In this case, the welding operation area may be an area including a portion where welding is performed by using the welding torch 200. The light index may correspond to data converted to compare the data about the degree of light described above with a particular threshold value and/or output data of a lighting unit as described below.

The processor 150 compares the light index with a preset threshold value (S13). When the light index is greater than the threshold value, the processor 150 outputs a first filtering index (S14), and displays a welding image generated based on welding image frames obtained through the camera unit 110 on the image display unit 120 (S15). The threshold value may correspond to an illuminance value of light generated at a welding light spot as welding starts. The illuminance value of the light generated at the welding light spot may vary depending on a type of welding and/or a state of welding, and the threshold value may be a value corresponding to a type of welding and/or a state of welding having a lowest illuminance value. However, the disclosure is not limited to thereto, and the threshold value may be a plurality of values each corresponding to a type of welding and/or a state of welding.

When the light index is greater than the threshold value, it means that welding starts, and thus the processor 150 provides a welding image to the image display unit 120 so that a user performs a welding operation by using the welding image obtained through the camera unit 110. To this end, the processor 150 adjusts a filtering index for light shield by the cartridge unit 130 to the first filtering index. The first filtering index corresponds to a filtering index for causing the cartridge unit 130 to be darkened, and the processor 150 may shield a considerable amount of welding light by adjusting the cartridge unit 130 through the preset first filtering index, thereby protecting an operator's eyes from high-brightness welding light. According to an embodiment of the disclosure, the first filtering index may be used to completely darken the cartridge unit 130 so that external light is blocked from being introduced into the main body 160. In addition, in embodiments, a mechanical light-shielding door that is selectively opened/closed may be optionally further provided on a front surface of the cartridge unit 130, and the user may further block introduction of welding light into the main body 160 by closing the light-shielding door during darkening of the cartridge unit 130.

In a state where the cartridge unit 130 is darkened, the user may see the welding image through the image display unit 120. Because the cartridge unit 130 that is the background of the image display unit 120 is darkened, the user may more clearly see an image formed on the image display unit 120. In this case, the image formed on the image display unit 120 may be formed in an area corresponding to a shield area of the cartridge unit 130. According to an embodiment of the disclosure, a shape of welding light transmitted through the cartridge unit 130 may overlap an image of welding light formed on the image display unit 120. Accordingly, a welding operation may be performed by using an image of welding light formed on the image display unit 120 without being disturbed by a shape of welding light finely introduced when the cartridge unit 130 is darkened by using the first filtering unit through the processor 150.

Because the user may check a welding situation by using an image through the camera unit 110 instead of the cartridge unit 130 while a welding operation is performed, the user may obtain visual information about not only a welding light spot but also a surrounding area of the welding light spot, and thus the user may relatively accurately and easily perform the welding operation when compared to a case where the welding operation is performed through the cartridge unit 130 that shows only the welding light spot.

When the light index is less than the threshold value, it is determined that a welding operation is not performed, and the processor 150 may calculate a second filtering index (S16) and may output the second filtering index to the cartridge unit 130, so that the user obtains visual information by using the cartridge unit 130 (S17).

The second filtering unit corresponds to a darkening index calculated to correspond to the light index less than the threshold value, and the light index and the second filtering unit may be pre-calculated so that a degree of light and a degree of darkening of the cartridge unit 130 have a preset combination, and may be stored in a table.

The processor 150 may continuously adjust the second filtering index by continuously reflecting a comparison result between the light index and the second filtering index. For example, when the light index is greater than the second filtering index, it means that external light is brightened, and thus the processor 150 may increase the degree of darkening by adjusting the second filtering index. When the light index is less than the second filtering index, the processor 150 may reduce the degree of darkening to ensure clearer visual recognition of an external environment. Therefore, the user may obtain more accurate visual information about the external environment and may avoid inconvenience when welding is not performed.

Optionally, the processor 150 may turn off the camera unit 110 and/or the image display unit 120, so that the user obtains visual information only through the cartridge unit 130. When welding is not performed, the user may communicate with a nearby colleague, may move, or may perform another operation. In this case, because the user may obtain visual information only through the cartridge unit 130, not the camera unit 110, the user may naturally obtain visual information without feeling uncomfortable and may more rapidly respond to nearby risk factors.

Accordingly, the welding information providing device according to embodiments of the disclosure may obtain optimal visual information according to an operation situation and/or a surrounding situation.

Although the main body 160 has a structure surrounding a user's head to a certain extent in the above embodiments of the disclosure, the disclosure is not limited thereto, and the main body 160 may have any of various structures such as a structure covering only the user's face or a goggles or glasses-type structure the user may wear.

In addition, although the camera unit 110 includes two cameras in the above embodiments of the disclosure, the disclosure is not limited thereto, and the camera unit 110 may include only one camera.

FIG. 9 is a view for describing an example where a camera obtains an image according to an embodiment of the disclosure.

In FIG. 9, the camera unit 110 includes two cameras. Referring to FIG. 9, a first camera and a second camera of the camera unit 110 may photograph a welding site by changing photographing conditions in a chronological order. In this case, the photographing conditions may include an ISO sensitivity, a gain, and/or a shutter speed.

A first frame a11 and a fifth frame a21 are obtained under a first photographing condition, a second frame a12 is obtained under a second photographing condition, and a third frame a14 is obtained under a third photographing condition. In the present embodiment of the disclosure, the first camera and the second camera perform photographing under the same photographing condition in the same frame.

For example, the first photographing condition may include a higher shutter speed than that of the second photographing condition, a high sensitivity, and a high gain, and the third photographing condition may include a lowest shutter speed and a low sensitivity. However, those are merely examples, and the camera unit 110 may obtain images under various photographing conditions.

Figure 10A:
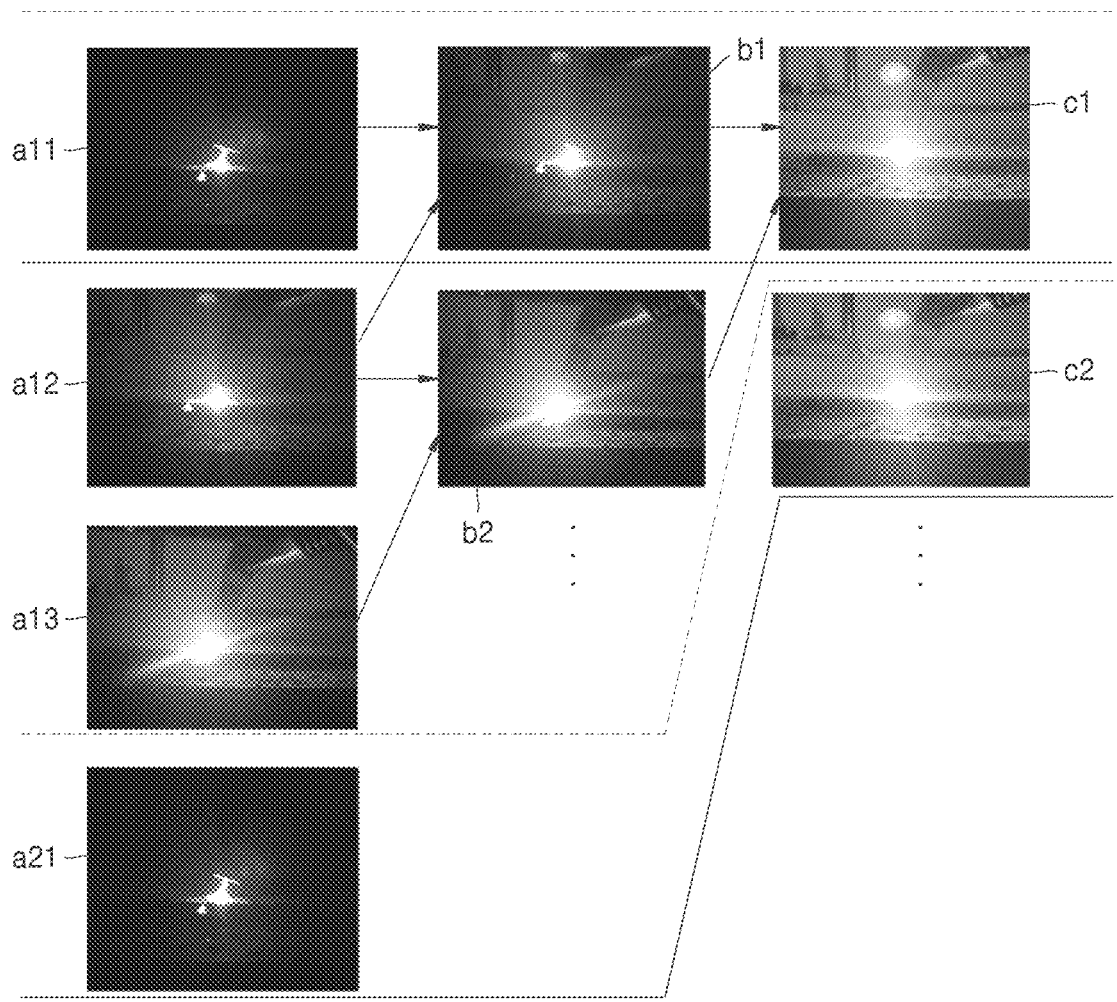
Figure 10B:
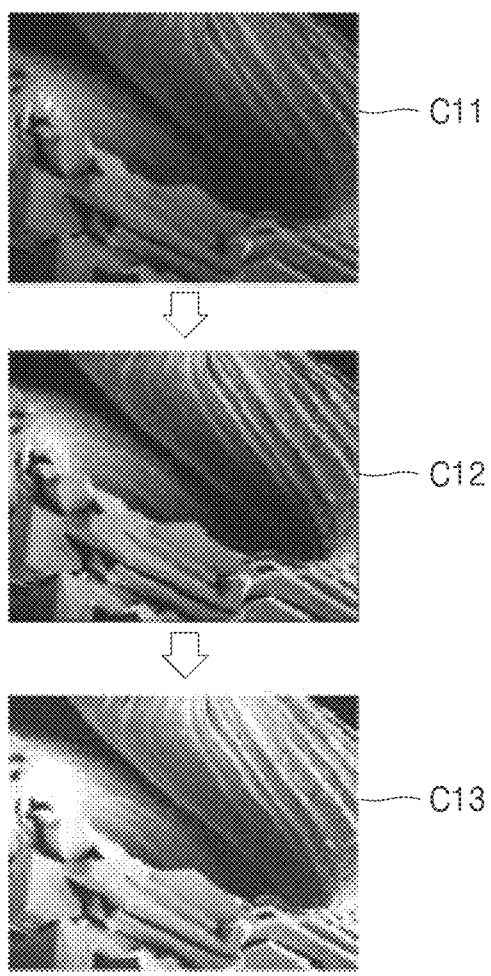

FIGS. 10A and 10B are views for describing an example where a processor synthesizes images obtained as in FIG. 9 and improves the quality of a synthesized image according to an embodiment of the disclosure.

The processor 150 according to an embodiment of the disclosure may synthesize images based on a preset number of frames. In this case, the number of frames for one synthesized image may be set by an operator or may be set at the time of release.

The processor 150 of FIG. 10A may generate a welding image, which is a synthesized image, based on three frames. In detail, the processor 150 may obtain a first intermediate synthesized image b1 by synthesizing the first frame a11 and the second frame a12. Also, the processor 150 may obtain a second intermediate synthesized image b2 by synthesizing the second frame a12 and the third frame a13.

The processor 150 may obtain a first synthesized image c1 by synthesizing the first intermediate synthesized image b1 and the second intermediate synthesized image b2.

Similarly, the processor 150 may synthesize a third intermediate synthesized image by synthesizing the third frame a13 and a fourth frame, and may obtain a second synthesized image c2 by synthesizing the second intermediate synthesized image b2 and the third intermediate synthesized image.

As described above, according to an embodiment of the disclosure, a high-quality synthesized image may be obtained by synthesizing images taken through various photographing conditions in a high dynamic photography (HDR) method. An operator may easily identify a surrounding portion other than a portion adjacent to a welding light spot by using the high-quality synthesized image. In embodiments, in the related art, because welding light is overwhelmingly brighter than the surrounding portion, an operator may not easily identify a shape of a weld bead and a welding surrounding environment. However, according to the welding system 10 of the disclosure, even a beginner operator may easily identify the weld bead and the welding surrounding environment by using a high-quality image.

The processor 150 may perform synthesis operations of the first synthesized image c1 and the second synthesized image c2 in parallel. According to an embodiment of the disclosure, the processor 150 may obtain a plurality of synthesized images at the same speed as a speed at which frames are obtained through the camera unit 110, by performing parallel image synthesis with a difference of one frame.

FIG. 10B is a view illustrating an example where the processor 150 performs a contrast enhancement on a synthesized image according to an embodiment of the disclosure.

Referring to FIG. 10B, the processor 150 may perform a contrast enhancement on an obtained synthesized image. For example, the processor 150 may perform additional contrast enhancement on an obtained first synthesized image c11 to obtain a second synthesized image c12 and a third synthesized image c13.

As described above, through additional contrast enhancement on a synthesized image, a contrast ratio may be increased and a light state of a welding helmet may be clearly identified.

Figure 11:
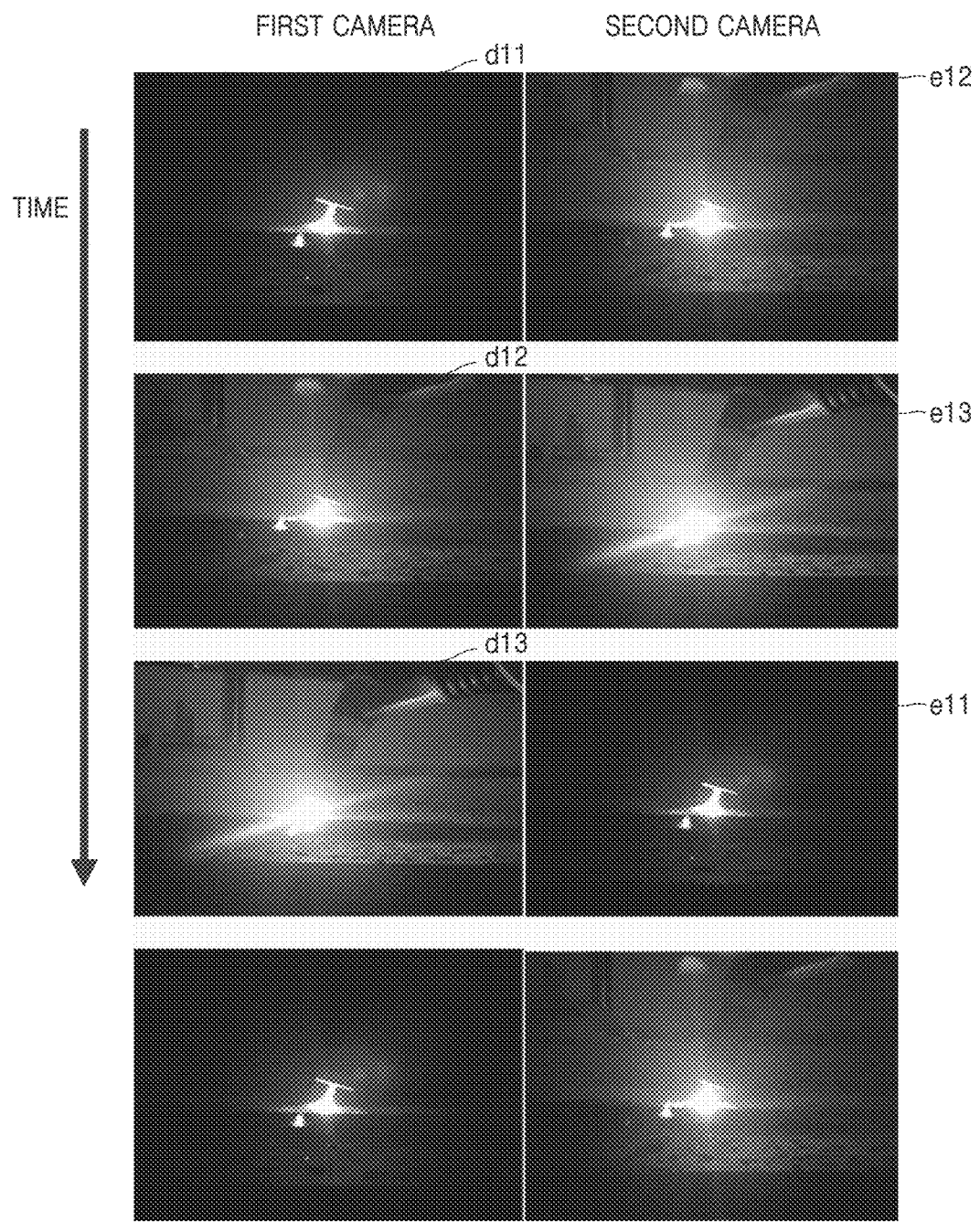
FIG. 11 is a view for describing an example where a plurality of cameras obtain images according to another embodiment of the disclosure.

FIG. 11 is a view for describing an example where a plurality of cameras obtain images according to an embodiment of the disclosure.

Referring to FIG. 11, a first camera and a second camera may photograph a welding situation under different photographing conditions in a frame of the same time.

For example, a first frame d11 of the first camera and a third frame e11 of the second camera may be obtained under a first photographing condition. A second frame d12 of the first camera and a first frame e12 of the second camera may be obtained under a second photographing condition, a third frame d13 of the first camera and a second frame e13 of the second camera may be obtained under a third photographing condition. In the present embodiment of the disclosure the first camera and the second camera perform photographing under different photographing conditions in the same frame.

For example, the first photographing condition may include a higher shutter speed than that of the second photographing condition, a high sensitivity, and a high gain, and the third photographing condition may include a lowest shutter speed and a low sensitivity. However, those are merely examples, and the camera unit 110 may obtain images under various photographing conditions.

Figure 12:
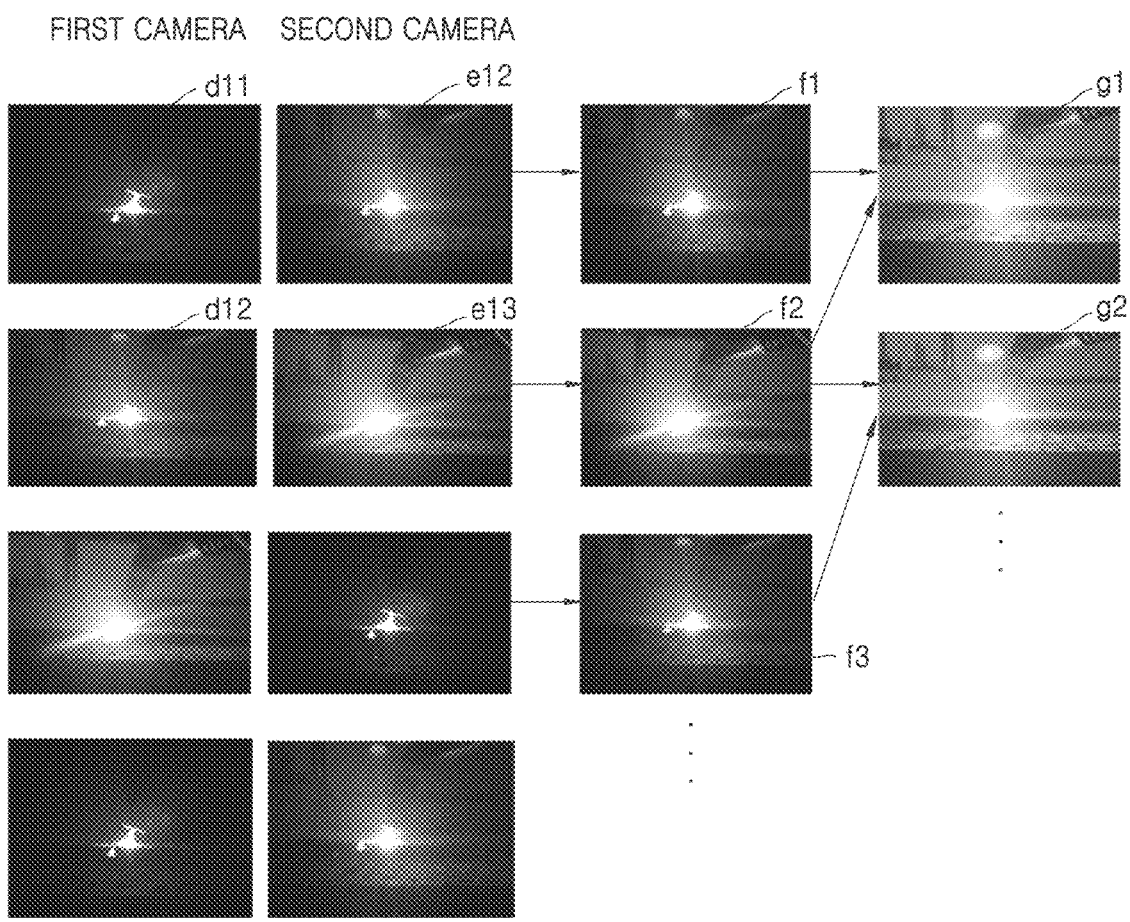
FIG. 12 is a view for describing a method of synthesizing images obtained in FIG. 11.

FIG. 12 is a view for describing a method of synthesizing images obtained in FIG. 11.

Referring to FIG. 12, the processor 150 may obtain a first intermediate synthesized image f1 by synthesizing the first frame d11 of the first camera and the first frame e11 of the second camera. Also, the processor 150 may obtain a second intermediate synthesized image f2 by synthesizing the second frame d12 of the first camera and the second frame e13 of the second camera.

The processor 150 may generate a first synthesized image g1 by synthesizing the first intermediate synthesized image f1 and the second intermediate synthesized image f2. Similarly, the processor 150 may obtain a second synthesized image g2 by synthesizing the second intermediate synthesized image f2 and a third intermediate synthesized image f3. The processor 150 may obtain a third synthesized image in the same manner.

As described above, according to embodiments of the disclosure, welding light in a welding image may be easily identified by synthesizing images obtained under various photographing conditions in an HDR method.

The processor 150 may perform synthesis operations of the first synthesized image g1 and the second synthesized image g2 in parallel. According to embodiments of the disclosure, the processor 150 may obtain a plurality of synthesized images at the same speed as a speed at which frames are obtained through the camera unit 110, by performing image synthesis in parallel at the same time as the first camera and the second camera obtain the frames.

According to an embodiment of the disclosure, the processor 150 may display a synthesized image only on one side of the image display unit 120 including a binocular display. For example, a synthesized image obtained by synthesizing images obtained through the first camera in a method of FIG. 10A may be displayed on a display corresponding to the first camera from among eyepiece displays. A synthesized image synthesized in a method of FIG. 11 may be displayed on a display corresponding to the second camera from among the eyepiece displays. Accordingly, a three-dimensional effect may be provided by providing a welding image in which welding light of a welding helmet is corrected in an HDR method on only one display from among the eyepiece displays.

In FIGS. 9 through 12, a welding site image or a welding image frame is obtained by changing a photographing condition of the camera unit 110 for each frame. However, according to another embodiment of the disclosure, the processor 150 of the disclosure may change a light-shielding degree of the cartridge unit 130 based on sensing information about an intensity of welding light obtained through the sensor unit 140. In this case, when the camera unit 110 is located inside the cartridge unit 130, a welding image frame may be obtained by changing a light-shielding degree of the cartridge unit 130 provided on a front portion of a camera.

In this case, the processor 150 may obtain the frames a11 to a13, a21, d11 to d13, and e11 to e13 having different contrast ratios as shown in FIGS. 9 to 12 by changing a light-shielding degree, while maintaining the same photographing condition of the camera unit 110.

Figure 13:
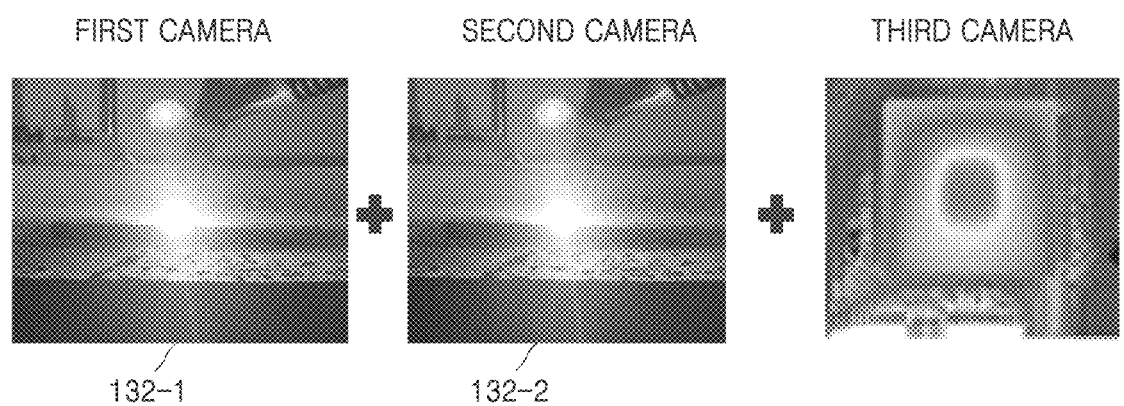
FIG. 13 is a view for describing a method of providing an image to a display unit according to another embodiment of the disclosure.

FIG. 13 is a view for describing a method of providing a welding image to an image display unit according to another embodiment of the disclosure.

Referring to FIG. 13, the camera unit 110 according to an embodiment may include a first camera, a second camera, and a third camera. An image display unit may include a first eyepiece display 132-1 and a second eyepiece display 132-2. in this case, the first camera may be a camera corresponding to the first eyepiece display 132-1, the second camera may be a camera corresponding to the second eyepiece display 132-2, and the third camera may be a thermal imaging camera.

The first eyepiece display 132-1 and the second eyepiece display 132-2 may display a high-quality synthesized image using an HDR method based on images obtained by the first camera and the second camera.

According to an embodiment of the disclosure, the processor 150 may obtain a thermal synthesized image obtained by additionally synthesizing a thermal image obtained by the third camera to the high-quality synthesized image. The first eyepiece display 132-1 and the second eyepiece display 132-2 may each display the thermal synthesized image. In this case, the first eyepiece display 132-1 and the second eyepiece display 1322 may provide visual information about a welding temperature by using colors.

According to an embodiment of the disclosure, the first eyepiece display 132-1 may display different images. For example, an image to which the HDR method is not applied may be displayed on the first eyepiece display 132-1, and a synthesized image to which the HDR method is applied may be displayed on the second eyepiece display 132-2. Even in this case, the processor 150 may synthesize a thermal image for each of the image to which the HDR method is not applied and the synthesized image to which the HDR technique is applied, and the first eyepiece display 132-1 and the second eyepiece display 132-2 may control the image display unit 120 to display the synthesized image on each of the first eyepiece display 132-1 and the second eyepiece display 132-2.

Figure 14:
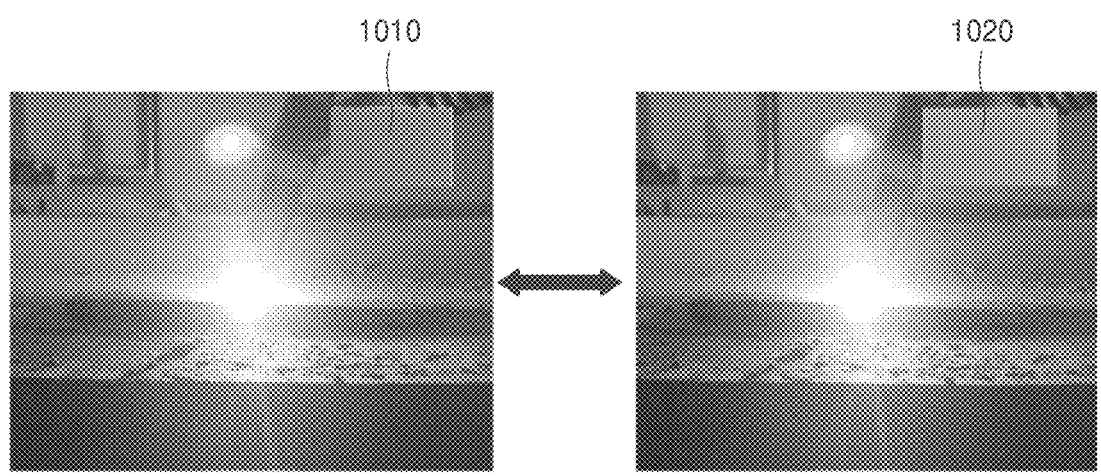
FIG. 14 is a view for describing an example where welding information is displayed according to another embodiment of the disclosure.

FIG. 14 is a view for describing an example where welding information is displayed according to another embodiment of the disclosure.

The processor 150 according to an embodiment of the disclosure may provide feedback on a state of a welding current and/or voltage in a welding power cable based on welding information sensed from the welding torch 200. In detail, referring to FIG. 14, the processor 150 may provide a UI for a current state on a portion of an image displayed on the image display unit 120. In this case, the UI may display information in a preset color using RGB.

For example, when the current and/or voltage state of the welding torch 200 is sensed as abnormal, the welding information providing device 100 according to an embodiment of the disclosure may display a red UI 1010 as visual feedback for warning, and in other oases, the welding information providing device 100 may display a green UI 1020.

In addition to the current state, the processor 150 may provide feedback on various welding information. For example, as shown in FIGS. 15A and 15B, the welding information providing device 100 may guide a UI for a welding direction of the welding torch 200 through visual feedback.

Figure 15A:
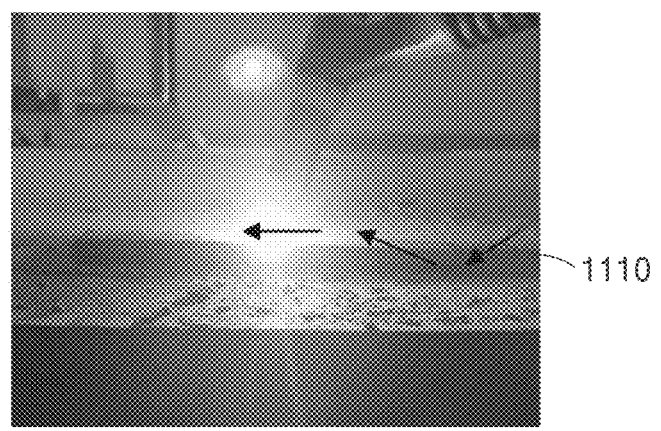
FIGS. 15A and 15B are views for describing an example where the welding information providing device guides a user interface (UI) for a welding direction of a torch through visual feedback.

Referring to FIG. 15A, the processor 150 may display information about a welding direction by using an arrow UI 1110. In detail, the processor 150 may display and provide each linear welding operation by using a linear arrow to an operator, based on information sensed by an acceleration sensor included in the welding torch 200.

Figure 15B:
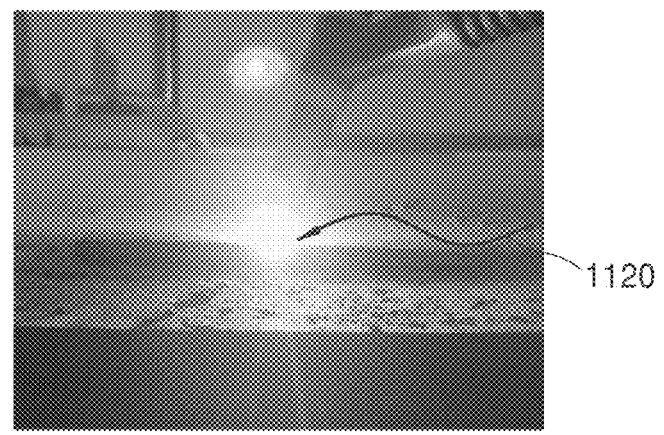

Alternatively, referring to FIG. 15B, the processor 150 may display information about a welding direction by using a curved arrow UI 1120. In detail, the processor 150 may display and provide a welding direction by using a curved arrow to the operator through the image display unit 120, based on information sensed by the acceleration sensor included in the welding torch 200.

However, those are merely examples, and the processor 150 may display a corresponding UI in a portion of the image display unit 120 based on sensing information including a welding temperature, a welding slope, a welding speed, and an interval between a base material and the welding torch 200 in a real-time welding operation sensed by at least one sensor 220 included in the welding torch 200.

For example, when sensing information about a welding temperature value is received, the processor 150 may display a UI corresponding to the welding temperature value in any of various methods, such as light, a vibration, or a message. In this case, the UI may be visual feedback displayed on the image display unit 120 or a portion of a display, or may be auditory feedback through a voice.

The sensing information about the welding temperature value may include whether a temperature of the base material exceeds a preset temperature range. Also, the sensing information about the welding temperature value may include a numerical value, a grade, a level, or the like corresponding to a temperature value of a welding helmet.

When it is determined that the temperature value of the base material exceeds the preset temperature range, the processor 150 according to an embodiment of the disclosure may guide an operator to stop an operation. When a temperature value of welding exceeds a preset temperature range, image quality may be deteriorated. Accordingly, the processor 150 may guide the operator to adjust the temperature value of the welding base material.

As another example, when sensing information about a welding speed value is received, the processor 150 may display a UI corresponding to the welding speed value. In this case, the UI may be visual feedback provided on the image display unit 120 or a display, or may be auditory feedback through a voice.

When it is determined that a welding speed of the welding torch 200 exceeds a normal range, the processor 150 may guide the operator to stop an operation through visual feedback. In this case, the visual feedback may involve providing an icon indicating danger on a portion of a display unit that is displaying an operation site.

As another example, the processor 150 may provide a UI so that the operator easily identifies a shape corresponding to a weld bead. In detail, when a shape of a weld bead is sensed, the processor 150 may overlap and display a UI for the shape of the weld bead on a high-quality synthesized image.

In this case, the shape of the weld bead may be obtained by sensing a residual temperature of the base material after a welding operation through a thermal imaging camera included in the welding information providing device 100. This is merely an example, and the welding information providing device 100 may obtain the shape of the weld bead by using various methods.

All of the embodiments described in the disclosure may be used in combination.

Although the welding information providing device 100 of the above embodiments of the disclosure is used in a welding operation, the disclosure is not limited to thereto. In embodiments, the welding information providing device 100 of the above embodiments may be implemented as an information providing device, and the information providing device may be used as an information providing device for medical and/or skin treatment while using the above configuration. In embodiments, when an operation using a camera image is performed, a user may easily obtain information about a surrounding environment by using a medical and/or skin treatment information providing device and may more safely and accurately perform the operation. Also, the information providing device of the disclosure may be used as an information providing device in various operations using camera images.

According to embodiments of the disclosure, a high-quality image capable of easily identifying a welding surrounding environment in addition to a portion adjacent to welding light may be provided by synthesizing images obtained under various photographing conditions.

Also, according to an embodiment of the disclosure described above, welding quality may be improved by providing an efficient guiding to an operator with respect to a current welding operation state.

A user may obtain optimal visual information in response to an environment that may vary according to an operation condition.

Logical blocks, modules or units described in connection with embodiments disclosed herein can be implemented or performed by a computing device having at least one processor, at least one memory and at least one communication interface. The elements of a method, process, or algorithm described in connection with embodiments disclosed herein can be embodied directly in hardware, in a software module executed by at least one processor, or in a combination of the two. Computer-executable instructions for implementing a method, process, or algorithm described in connection with embodiments disclosed herein can be stored in a non-transitory computer readable storage medium.

The scope of the disclosure is not limited by these effects.

R should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A welding information providing device comprising:
   a cartridge unit located on a main body and configured to selectively shield welding light;
   at least one camera unit located on the main body to face outward and configured to obtain a welding image frame of a welding operation;
   a sensor unit located outside the main body;
   an image display unit located between the cartridge unit and a user inside the main body; and
   a processor configured to communicate with the cartridge unit, the at least one camera unit, and the image display unit to provide a welding image generated through the welding image frame to the image display unit; and
   the at least one camera unit comprising:
      a first camera located at a first region of the main body and configured to generate two or more first welding image frames of the welding image frame under a first capturing condition;
      a second camera located at a second region of the main body and configured to generate two or more second welding image frames of the welding image frame under a second capturing condition different from the first capturing condition, the second region being different from the first region; and
      a third camera configured to generate a thermal image of the welding image frame, and
   the processor further configured to:
      synthesize the two or more first welding image frames to generate a first synthesized image;
      synthesize the two or more second welding image frames to generate a second synthesized image;
      synthesize the first synthesized image and the thermal image to generate a first synthesized thermal image;
      synthesize the second synthesized image and the thermal image to generate a second synthesized thermal image; and
      control the image display unit to display the first synthesized thermal image on a first area of the image display unit and display the second synthesized thermal image on a second area of the image display unit different from the first area.

2. The welding information providing device of claim 1, wherein the sensor unit comprises a module configured to sense welding information, and
   wherein the processor is configured to control the image display unit to provide a guide corresponding to the welding information based on the welding information sensed by the sensor unit.

3. The welding information providing device of claim 2, wherein at least a part of the sensor unit is located on a welding torch.

4. The welding information providing device of claim 2, wherein the welding information comprises at least one of welding speed information, welding direction information, welding temperature information, and distance information between a welding base material and a welding torch.

5. The welding information providing device of claim 1, wherein the cartridge unit comprises a shield area for shielding the welding light, and the image display unit comprises an image display area where an image is displayed to the user, and
   wherein the shield area and the image display area overlap each other for the user's eye.

6. The welding information providing device of claim 1, wherein the image display unit is configured to transmit light therethrough.

7. The welding information providing device of claim 2, wherein the cartridge unit comprises a shield area for shielding the welding light, and the image display unit comprises an image display area where an image is displayed to the user, and
   wherein the shield area and the image display area overlap each other for the user's eye.

8. The welding information providing device of claim 2, wherein the image display unit is configured to transmit light therethrough.

9. The welding information providing device of claim 3, wherein the cartridge unit comprises a shield area for shielding the welding light, and the image display unit comprises an image display area where an image is displayed to the user, and
   wherein the shield area and the image display area overlap each other for the user's eye.

10. The welding information providing device of claim 3, wherein the image display unit is configured to transmit light therethrough.

11. The welding information providing device of claim 4, wherein the cartridge unit comprises a shield area for shielding the welding light, and the image display unit comprises an image display area where an image is displayed to the user, and
    wherein the shield area and the image display area overlap each other for the user's eye.

12. The welding information providing device of claim 4, wherein the image display unit is configured to transmit light therethrough.

* * * * *

UNITED STATES PATENT AND TRADEMARK OFFICE
CERTIFICATE OF CORRECTION

PATENT NO. : 12,064,834 B2
APPLICATION NO. : 17/030828
DATED : August 20, 2024
INVENTOR(S) : Moon Young Huh It is certified that error appears in the above-identified patent and that said Letters Patent is hereby corrected as shown below:

In the Specification

Column 1, Line 44, delete "Information" and insert -- information --.

Column 4, Line 30, delete "disclosure," and insert -- disclosure. --.

Column 4, Line 54, delete "data," and insert -- data. --.

Column 7, Line 30, delete "he" and insert -- be --.

Column 7, Line 31, delete "161" and insert -- 161, --.

Column 8, Line 20, delete "Information" and insert -- information --.

Column 9, Line 32, delete "fight" and insert -- light --.

Column 9, Line 56, delete "(SSID))" and insert -- (SSID) --.

Column 12, Line 37, delete "Meld" and insert -- field --.

Column 13, Line 12 (approx.), delete "dose" and insert -- close --.

Column 17, Line 11, delete "disclosure" and insert -- disclosure, --.

Column 18, Line 21, delete "in" and insert -- In --.

Column 18, Line 37, delete "1322" and insert -- 132-2 --.

Column 19, Line 1, delete "oases," and insert -- cases, --.

Signed and Sealed this
Twenty-sixth Day of November, 2024

Katherine Kelly Vidal
*Director of the United States Patent and Trademark Office*

CERTIFICATE OF CORRECTION (continued)
U.S. Pat. No. 12,064,834 B2

Column 20, Line 57, delete "R" and insert -- It --.

In the Claims

Column 21, Line 14, Claim 1, delete "unit; and" and insert -- unit, --.